United States Patent
Zack et al.

(10) Patent No.: US 9,539,259 B2
(45) Date of Patent: Jan. 10, 2017

(54) COMPOUNDS AND METHODS OF USE THEREOF FOR TREATING NEURODEGENERATIVE DISORDERS

(71) Applicant: THE JOHNS HOPKINS UNIVERSITY, Baltimore, MD (US)

(72) Inventors: Donald J. Zack, Baltimore, MD (US); Derek Stuart Welsbie, Lutherville-Timonium, MD (US); Zhiyong Yang, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 99 days.

(21) Appl. No.: 14/403,523

(22) PCT Filed: May 23, 2013

(86) PCT No.: PCT/US2013/042367
§ 371 (c)(1),
(2) Date: Nov. 24, 2014

(87) PCT Pub. No.: WO2013/177367
PCT Pub. Date: Nov. 28, 2013

(65) Prior Publication Data
US 2015/0164906 A1  Jun. 18, 2015

Related U.S. Application Data

(60) Provisional application No. 61/680,931, filed on Aug. 8, 2012, provisional application No. 61/650,613, filed on May 23, 2012.

(51) Int. Cl.
| | | |
|---|---|---|
| *A61K 31/535* | (2006.01) | |
| *A61K 31/5377* | (2006.01) | |
| *A61K 45/06* | (2006.01) | |
| *A61K 31/4439* | (2006.01) | |
| *A61K 31/4545* | (2006.01) | |
| *A61K 31/47* | (2006.01) | |
| *A61K 31/496* | (2006.01) | |
| *A61K 31/506* | (2006.01) | |
| *A61K 31/517* | (2006.01) | |
| *G01N 33/573* | (2006.01) | |
| *C12Q 1/68* | (2006.01) | |

(52) U.S. Cl.
CPC ....... *A61K 31/5377* (2013.01); *A61K 31/4439* (2013.01); *A61K 31/4545* (2013.01); *A61K 31/47* (2013.01); *A61K 31/496* (2013.01); *A61K 31/506* (2013.01); *A61K 31/517* (2013.01); *A61K 45/06* (2013.01); *C12Q 1/6876* (2013.01); *G01N 33/573* (2013.01); *C12Q 2600/158* (2013.01); *G01N 2333/912* (2013.01); *G01N 2333/91205* (2013.01); *G01N 2800/16* (2013.01)

(58) Field of Classification Search
CPC ................................................ C07D 265/36
USPC ....................................................... 514/230.5
See application file for complete search history.

(56) References Cited

U.S. PATENT DOCUMENTS

2011/0172206 A1   7/2011   Zack et al.

FOREIGN PATENT DOCUMENTS

| CA | 2339539 A1 | 3/2000 |
|---|---|---|
| CA | 2606658 A1 | 4/2008 |
| EP | 2535339 A1 | 12/2012 |
| EP | 2769976 A1 | 8/2014 |
| WO | 2004000833 | 12/2003 |
| WO | 2005/123048 A2 | 12/2005 |
| WO | 2006068795 | 6/2006 |
| WO | 2006116301 | 11/2006 |
| WO | 2007056164 | 5/2007 |
| WO | 2007056221 | 5/2007 |
| WO | 2007/146824 A2 | 12/2007 |
| WO | 2008087458 A2 | 7/2008 |
| WO | 2009129187 | 10/2009 |
| WO | 2010017541 | 2/2010 |
| WO | 2010/141483 A2 | 12/2010 |
| WO | 2011050192 | 4/2011 |
| WO | 2011119777 | 9/2011 |
| WO | 2013/040801 A1 | 3/2013 |
| WO | 2013/188273 A1 | 12/2013 |
| WO | 2014/127214 A1 | 8/2014 |
| WO | 2014/204791 A1 | 12/2014 |

OTHER PUBLICATIONS

Kataoka et al. 2011. "Foretinib (GSK1363089), a multi-kinase inhibitor of MET and VEGFRs, inhibits growth of gastric cancer cell lines by blocking inter-receptor tyrosine kinase networks". Angiogenesis, vol. 15, No. 1, pp. 59-70.

Zillhardt et al. 2011. "Foretinib (GSK1363089), an orally available multikinase inhibitor of c-Met and VEGFR-2, blocks proliferation, induces anoikis, and impairs ovarian cancer metastasis". Clin Cancer Res., vol. 17, No. 12, pp. 4042-4051.

Qian et al. 2012. "I nhibition of tumor cell growth, invasion, and metastasis by EXEL-2880 (XL880, GSK1363089), a novel inhibitor of HGF and VEGF receptor tyrosine kinases". Invest New Drugs., vol. 30, No. 1, pp. 327-334.

Dufies et al. 2011. "Mechanism of action of the multikinase inhibitor Foretinib". Cell Cycle, vol. 10, No. 23, pp. 4138-4148.

(Continued)

*Primary Examiner* — Raymond Henley, III
(74) *Attorney, Agent, or Firm* — Ward and Smith, P.A.; Jeffrey W. Childers

(57) ABSTRACT

Compounds, compositions, kits and methods for treating conditions related to neurodegeneration or ocular disease, are disclosed.

38 Claims, 21 Drawing Sheets

(56) References Cited

OTHER PUBLICATIONS

Bowles et al. 2011. "Multi-targeted tyrosine kinase inhibitors in clinical development: focus on XL:-184 (cabozantinib)". Drugs Today (Barc), vol. 47, No. 11, pp. 857-868.
Yakes et al. 2011. "Cabozantinib (XL184), a novel MET and VEGFR2 inhibitor, simultaneously suppresses metastasis, angiogenesis, and tumor growth ". Mol Cancer Ther., vol. 10, No. 2, pp. 2298-2308.
Kurzrock et al. 2011. "Activity of XL184 (Cabozantinib), an oral tyrosine kinasinhibitor, in patients with medullary thyroid cancer". J Clin Oncol., vol. 29, No. 19, pp. 2660-2666.
Houvras et al. 2011. "Cabozantinib in medullary thyroid carcinoma: time to focus the spotlight on this rare disease". J Clin Oncol., vol. 29, No. 19, pp. 2616-2618.
Quigley et al. 2011. "Lack of neuroprotection against experimental glaucoma in c-Jun N-terminal kinase 3 knockout mice". Exp Eye Res., vol. 92, No. 4, pp. 299-305.
Yang & Zack. "What has gene expression profiling taught us about glaucoma?" Exp Eye Res., vol. 93, No. 2, pp. 191-195.
Petrs-Silva, H. et al. "Novel Properties of Tyrosine-mutant AAV2 Vectors in the Mouse Retina". Mol. Ther. 19, 293-301 (2011).
Monge Katia Sotelo et al ., "Optic neuropathy secondary to dasatinib in the treatment of a chronic myeloid leukemia case", Saudi Journal of Ophthalmology, Elsevier, Amsterdam, NL, vol. 29, No. 3, Jan. 7, 2015, pp. 227-231.
Extended European Search Report dated Dec. 16, 2015 for a corresponding EP Application No. 13793466.
Written Opinion of the International Searching Authority dated Aug. 23, 2013 for PCT/US2013/042367 with International Filing Date of May 23, 2013.
Barres, B. A., et al., Immunological, morphological, and electrophysiological variation among retinal ganglion cells purified by panning. Neuron 1, 791-803 (1988).
Bessero, A.-C., et al., Role of the c-Jun N-terminal kinase pathway in retinal excitotoxicity, and neuroprotection by its inhibition. J. Neurochem. 113, 1307-1318 (2010).
Bhattacharya MRC et al., (2012) A model of toxic neuropathy in *Drosophila* reveals a role for MORN4 in promoting axonal degeneration. J. Neurosci.32:5054-5061.
Bloom, J., et al., The requirement for Phr1 in CNS axon tract formation reveals the corticostriatal boundary as a choice point for cortical axons. Genes Dev. 21, 2593-2606 (2007).
Cohen P (2002) Protein kinases—the major drug targets of the twenty-first century? Nat. Rev. Drug Discov. 1:309-315.
Collins, C. A., et al., Highwire restrains synaptic growth by attenuating a MAP kinase signal. Neuron 51,57-69 (2006).
Danesh-Meyer, H. V. & Levin, L. A. Neuroprotection: extrapolating from neurologic diseases to the eye. American Journal of Ophthalmology 148, 186-191.e2 (2009).
Davies C, Tournier C (2012) Exploring the function of the JNK (c-Jun N-terminal kinase) signalling pathway in physiological and pathological processes to design novel therapeutic strategies. Biochem. Soc. Trans. 40:85-89.
Davis, M. I., et al., Comprehensive analysis of kinase inhibitor selectivity. Nat. Biotechnol. 29, 1046-1051 (2011).
Dimitriadi M et al., (2010) Conserved Genes Act as Modifiers of Invertebrate SMN Loss of Function Defects. PLoS. Genet. 6:e1001172.
Edwards, D. A., et al. Large porous particles for pulmonary drug delivery. Science 276, 1868-1871 (1997).
Fernandes, K. A., et al., JNK2 and JNK3 are major regulators of axonal injury-induced retinal ganglion cell death. Neurobiology of Disease (2012).
Ghosh, A. S. et al. DLK induces developmental neuronal degeneration via selective regulation of proapoptotic JNK activity. J. Cell Biol. 194,751-764 (2011).
Hammarlund M, et al., (2009) Axon Regeneration Requires a Conserved MAP Kinase Pathway. Science 323:802-806.
Harrington EA, et al., (2004) VX-680, a potent and selective small-molecule inhibitor of the Aurora kinases, suppresses tumor growth in vivo. Nat. Med. 10:262-267.
Hisanaga S-I, Endo R (2010) Regulation and role of cyclin-dependent kinase activity in neuronal survival and death. J Neurochem 115:1309-1321.
Inglese, J. et al. Quantitative high-throughput screening: a titration-based approach that efficiently identifies biological activities in large chemical libraries. Proceedings of the National Academy of Sciences of the United States of America 103,11473-11478 (2006).
Itoh A, et al., (2009) Impaired regenerative response of primary sensory neurons in ZPK/DLK gene-trap mice. Biochem Biophys. Res. Commun. 383:258-262.
Itoh, A. et al. ZPK/DLK, a mitogen-activated protein kinase kinase kinase, is a critical mediator of programmed cell death of motoneurons. J. Neurosci. 31, 7223-7228 (2011).
Karaman, M. W. et al. A quantitative analysis of kinase inhibitor selectivity. Nat. Biotechnol. 26, 127-132 (2008).
Lackey, K. et al. The discovery of potent cRaf1 kinase inhibitors. Bioorganic & Medicinal Chemistry Letters 10,223-226 (2000).
Levkovitch-Verbin, H. et al. Translimbal laser photocoagulation to the trabecular meshwork as a model of glaucoma in rats. Investigative Ophthalmology & Visual Science 43, 402-410 (2002).
Li Y, et al., (1999) Experimental induction of retinal ganglion cell death in adult mice. Investigative Ophthalmology & Visual Science 40:1004-1008.
Limb GA, Martin KR, the Sixth ARVO/Pfizer Ophthalmics Research Institute Conference Working Group (2011) Current Prospects in Optic Nerve Protection and Regeneration: Sixth ARVO/Pfizer Ophthalmics Research Institute Conference. Investigative Ophthalmology & Visual Science 52:5941-5954.
Merritt SE et al. (1999) The mixed lineage kinase DLK utilizes MKK7 and not MKK4 as substrate. J. Biol. Chem. 274:10195-10202.
Miller, B. R. et al. A dual leucine kinase-dependent axon self-destruction program promotes Wallerian degeneration. Nat. Neurosci. 12, 387-389 (2009).
OFarrell, A. et al. SU11248 is a novel FLT3 tyrosine kinase inhibitor with potent activity in vitro and in vivo. Blood 101, 3597-3605 (2003).
Pavlidis M, et al., (2000) Photoreceptor degeneration in the RCS rat attenuates dendritic transport and axonal regeneration of ganglion cells. Investigative Ophthalmology & Visual Science 41:2318-2328.
Petrs-Silva, H. et al. High-efficiency transduction of the mouse retina by tyrosine-mutant AAV serotype vectors. Mol. Ther. 17, 463-471 (2009).
Quigley, H. A. & Broman, A. T. The number of people with glaucoma worldwide in 2010 and 2020. Br J Ophthalmol 90, 262-267 (2006).
Ribas, V. T., et al., Early c-Jun N-terminal kinase-dependent phosphorylation of activating transcription factor-2 is associated with degeneration of retinal ganglion cells. Neuroscience 180, 64-74 (2011).
Robitaille, K. et al. Tissue transglutaminase triggers oligomerization and activation of dual leucine zipper-bearing kinase in calphostin C-treated cells to facilitate apoptosis. Cell Death Differ. 11, 542-549 (2004).
Satoh K, Fukumoto Y, Shimokawa H (2011) Rho-kinase: important new therapeutic target in cardiovascular diseases. Am. J. Physiol. Heart Circ. Physiol. 301:H287-96.
Schulte J, et al., (2011) High-Content Chemical and RNAi Screens for Suppressors of Neurotoxicity in a Huntington's Disease Model. PLoS One 6:e23841.
Scott DL (2011) Role of spleen tyrosine kinase inhibitors in the management of rheumatoid arthritis. Drugs 71:1121-1132.
Sharma P, et al., (2012) High-throughput screening in primary neurons. Meth. Enzymol. 506:331-360.
Shin JE et al. (2012) Dual Leucine Zipper Kinase Is Required for Retrograde Injury Signaling and Axonal Regeneration. Neuron 74:1015-1022.
Subramaniam S, Unsicker K (2010) ERK and cell death: ERK1/2 in neuronal death. FEBS J 277:22-29.

(56) References Cited

OTHER PUBLICATIONS

Sun, H. et al. Protective effect of a JNK inhibitor against retinal ganglion cell loss induced by acute moderate ocular hypertension. Mol. Vis. 17,864-875 (2011).

Tanaka M, et al. (2009) Transfer of small interfering RNA by single-cell electroporation in cerebellar cell cultures. Journal of neuroscience methods 178:80-86.

Tanaka M, et al., (2011) Long-Term Gene-Silencing Effects of siRNA Introduced by Single-Cell Electroporation into Postmitotic CNS Neurons. Neurochem Res 36:1482-1489.

Tang BC, et al., (2010) Enhanced efficacy of local etoposide delivery by poly(ether-anhydride) particles against small cell lung cancer in vivo. Biomaterials 31:339-344.

Tournier C, et al. (1997) Mitogenactivated protein kinase kinase 7 is an activator of the c-Jun NH2-terminal kinase. Proceedings of the National Academy of Sciences of the United States of America 94:7337-7342.

Tu W et al. (2010) DAPK1 Interaction with NMDA Receptor NR2B Subunits Mediates Brain Damage in Stroke. Cell 140:222-234.

Wang JT, et al., Barres Axon degeneration: Molecular mechanisms of a self-destruction pathway.

Weston CR, Davis RJ (2007) The JNK signal transduction pathway. Curr. Opin. Cell Biol. 19:142-149.

Xiong X et al. (2010) Protein turnover of the Wallenda/DLK kinase regulates a retrograde response to axonal injury. J. Cell Biol. 191:211-223.

Yan D, et al., (2009) The DLK-1 Kinase Promotes mRNA Stability and Local Translation in C. elegans Synapses and Axon Regeneration. Cell 138:1005-1018.

Yang Z et al. (2007) Changes in gene expression in experimental glaucoma and optic nerve transection: the equilibrium between protective and detrimental mechanisms. Investigative Ophthalmology & Visual Science 48:5539-5548.

Zolotukhin, S. et al. Production and purification of serotype 1, 2, and 5 recombinant adeno-associated viral vectors. Methods 28, 158-167 (2002).

a

SR8165 b c

COMPOUNDS AND METHODS OF USE THEREOF FOR TREATING NEURODEGENERATIVE DISORDERS

CROSS-REFERENCE TO RELATED APPLICATIONS

This application is a 35 U.S.C. §371 U.S. national phase entry of International Application No. PCT/US2013/042367 having an international filing date of May 23, 2013, which claims the benefit of priority to U.S. Provisional Application No. 61/650,613, filed May 23, 2012, and to U.S. Provisional Application No. 61/680,931, filed Aug. 8, 2012, the entire disclosures of which are incorporated herein in their entireties.

FEDERALLY SPONSORED RESEARCH OR DEVELOPMENT

This invention was made with government support under EY022078 and EY019737 awarded by the National Institutes of Health. The government has certain rights in the invention.

BACKGROUND

Neurodegenerative disorders afflict numerous patients throughout the world and can be devastating to patients and caregivers. Such disorders also can result in great financial burdens, with annual costs currently exceeding several hundred billion dollars in the United States alone. Current treatments for such disorders often are inadequate. Further, many such disorders are age-related, and thus their incidence is rapidly increasing as demographics trend toward an aging population. For example, glaucoma, a disease, disorder, or condition that results in damage to the optic nerve, is a major cause of vision loss and blindness, especially in the elderly. Although various treatments for glaucoma exist, many such treatments are of limited efficacy and/or have significant side effects. Reduction of intraocular pressure, generally through pharmacologic, laser, or surgical intervention, is presently the mainstay of glaucoma therapy. Such therapies, however, often are only partially effective and generally cannot restore neuronal cell function once such function has been lost.

SUMMARY

In some aspects, the presently disclosed subject matter provides a method for treating or preventing a neurodegenerative disease, disorder, or condition in a subject in need thereof, the method comprising administering to the subject a therapeutically effective amount of a compound of Formula (I), or a pharmaceutically acceptable salt, hydrate, or prodrug thereof, thereby treating or preventing the neurodegenerative disease, disorder, or condition:

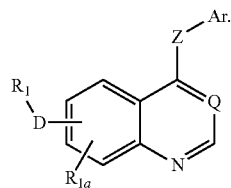

(I)

In some aspects, the compound of Formula I is a compound of formula A-B—C as defined in paragraphs [0095-0165] of U.S. Patent Application Publication No. US20070054928. In more particular aspects, the compound of Formula (I) is a compound of Formula (XI) as disclosed in paragraphs [0109-0117] of U.S. Patent Application Publication No. US20070054928:

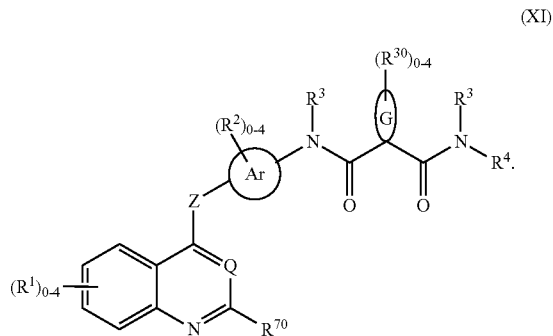

(XI)

In yet more particular aspects, the compound of Formula (I) is a compound of Formula (XIIIa) or (XIIIb) as disclosed in paragraphs [0118-0126] of U.S. Patent Application Publication No. US20070054928:

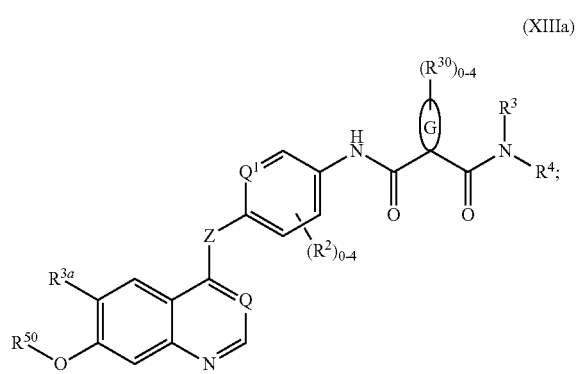

(XIIIa)

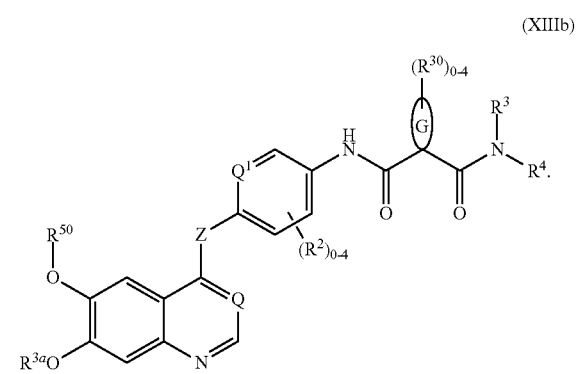

(XIIIb)

In some aspects, the compound of Formula (I) is a compound of Formula (XIVa) or Formula (XIVb), as disclosed in paragraphs [0126-0165] of U.S. Patent Application Publication No. US20070054928:

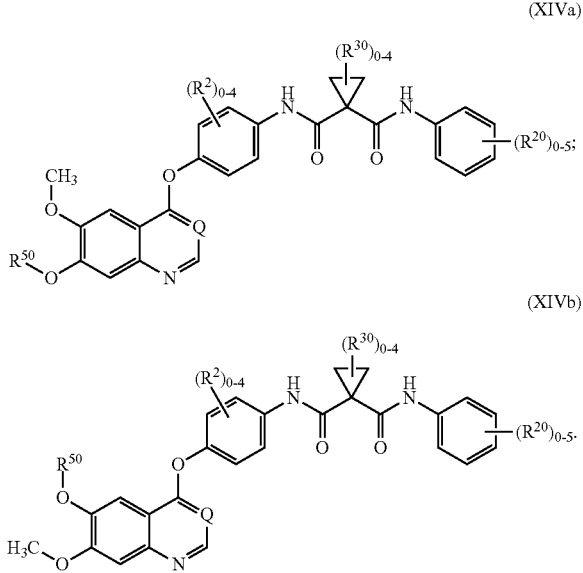

In particular aspects, the compound of Formula (XIVa) is foretinib (also referred to as XL-880 or GSK1363069). In yet other particular aspects, the compound of Formula (XIVb) is cabozantinib (also referred to as XL-184).

In yet other aspects, the compound is crizotinib, or a related compound. In some aspects, the compound is KW-2449. In yet other aspects, the compound is bosutinib. In yet other aspects, the compound is axitinib. In yet further aspects, the compound is dasatinib, also referred to as BMS-354825 or Sprycel®, or a related compound.

In particular aspects, the neurodegenerative disease, disorder, or condition is an ocular-related neurodegeneration, such as glaucoma, retinitis pigmentosa (RP), and age-related macular degeneration (AMD).

In still other aspects, the presently disclosed subject matter provides a method for promoting retinal ganglion cell (RGC) and/or photoreceptor cell survival by contacting a RGC or photoreceptor cell with a compound of Formula (I), or other compounds disclosed herein, in an amount sufficient to promote RGC or photoreceptor cell survival.

In particular aspects, the compound of Formula (I), or other compounds disclosed herein, promotes RGC or photoreceptor cell survival by inhibiting the dual-leucine zipper kinase (DLK) (MAP3K12) pathway and/or the leucine zipper-bearing kinase (LZK) (MAP3K13) pathway.

In other aspects, the presently disclosed subject matter provides a method for identifying injury to an RGC or photoreceptor cell by measuring levels of DLK or LZK protein in the RGC or photoreceptor cell and comparing the levels of DLK or LZK protein in the RGC or photoreceptor cell to the levels of DLK or LZK protein in a control RGC or photoreceptor cell, wherein a significant difference between the levels of DLK or LZK protein in the RGC or photoreceptor cell and the levels of DLK or LZK protein in the control RGC or photoreceptor cell is indicative of injury to the RGC or photoreceptor cell. In addition, a method for identifying injury to an RGC or photoreceptor cell in a subject is provided comprising obtaining a sample from a subject, measuring levels of DLK or LZK protein in the sample and comparing the levels of DLK or LZK protein in the sample to the levels of DLK or LZK protein in a control sample, wherein a significant difference between the levels of DLK or LZK protein in the sample and the levels of DLK or LZK protein in the control sample is indicative of injury to a RGC or photoreceptor cell in the subject. In particular embodiments, the sample is selected from the group consisting of the vitreous, the aqueous of the eye, and serum.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
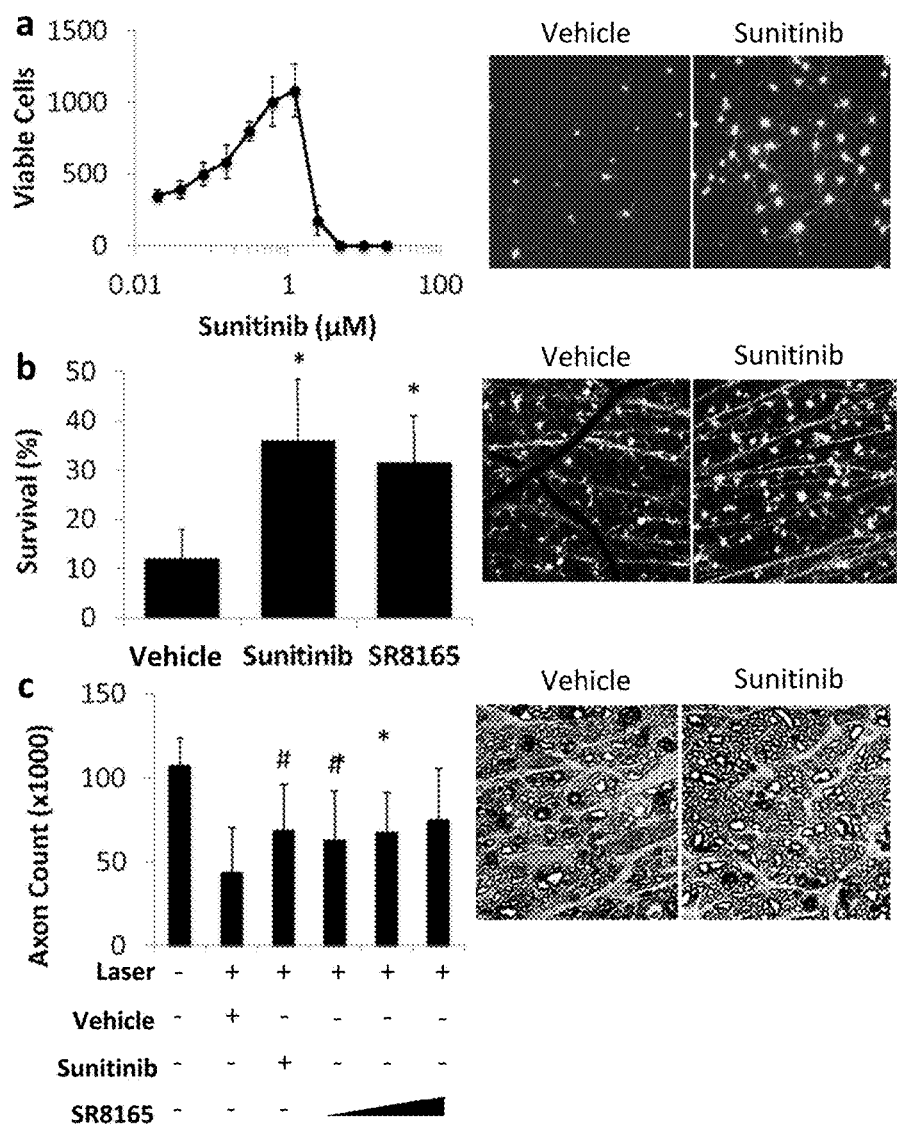
Figure 3A:
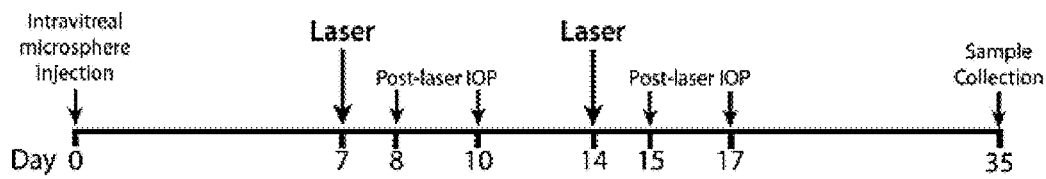
Figure 3B:
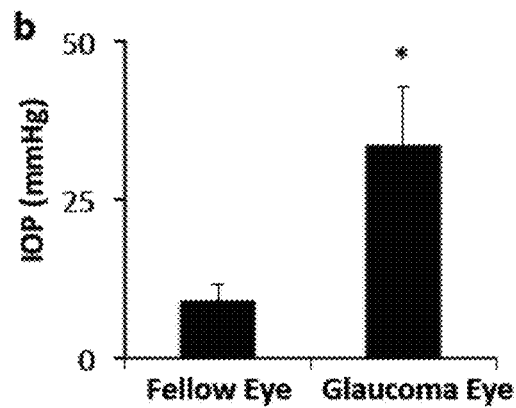
Figure 3C:
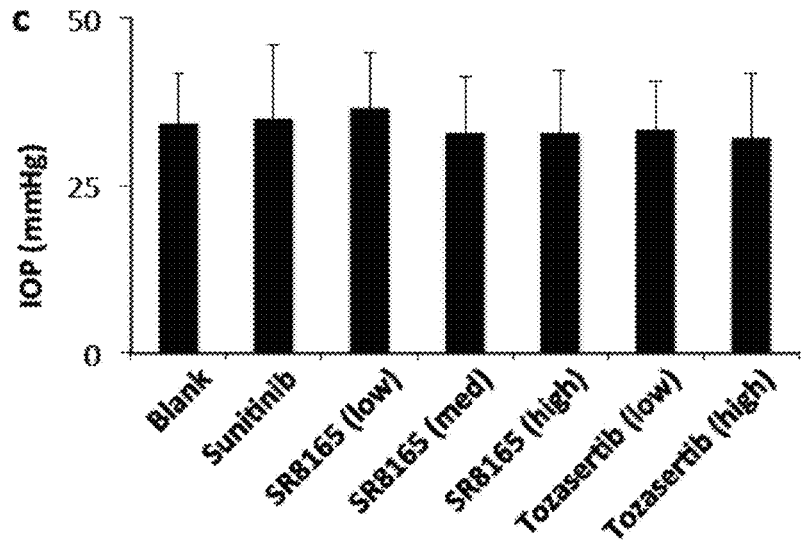
Figure 4:
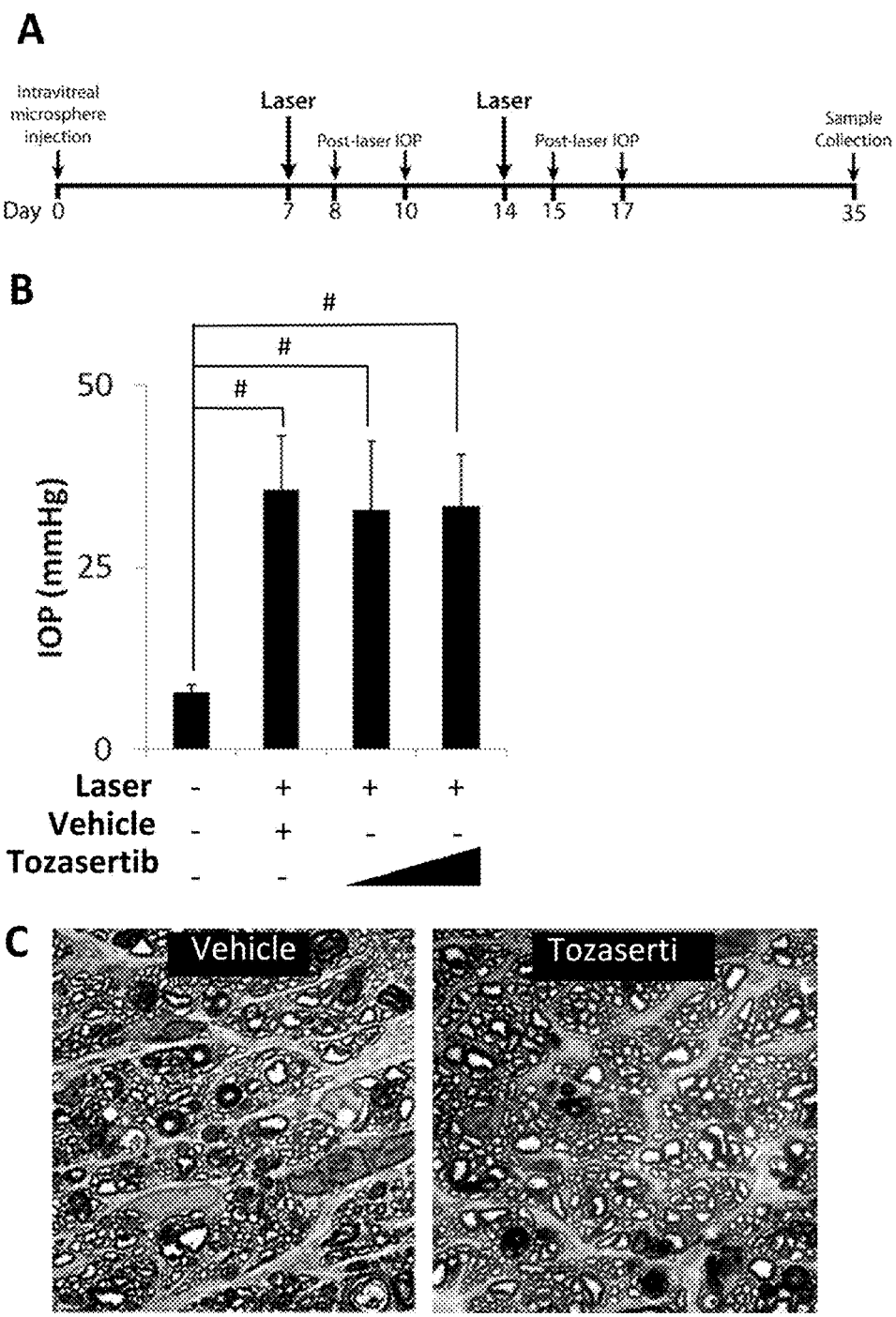
Figure 8:
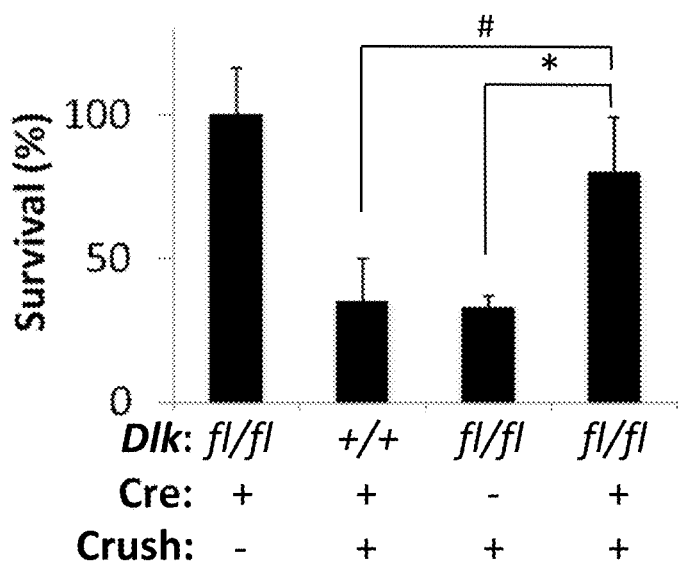
Figure 9:
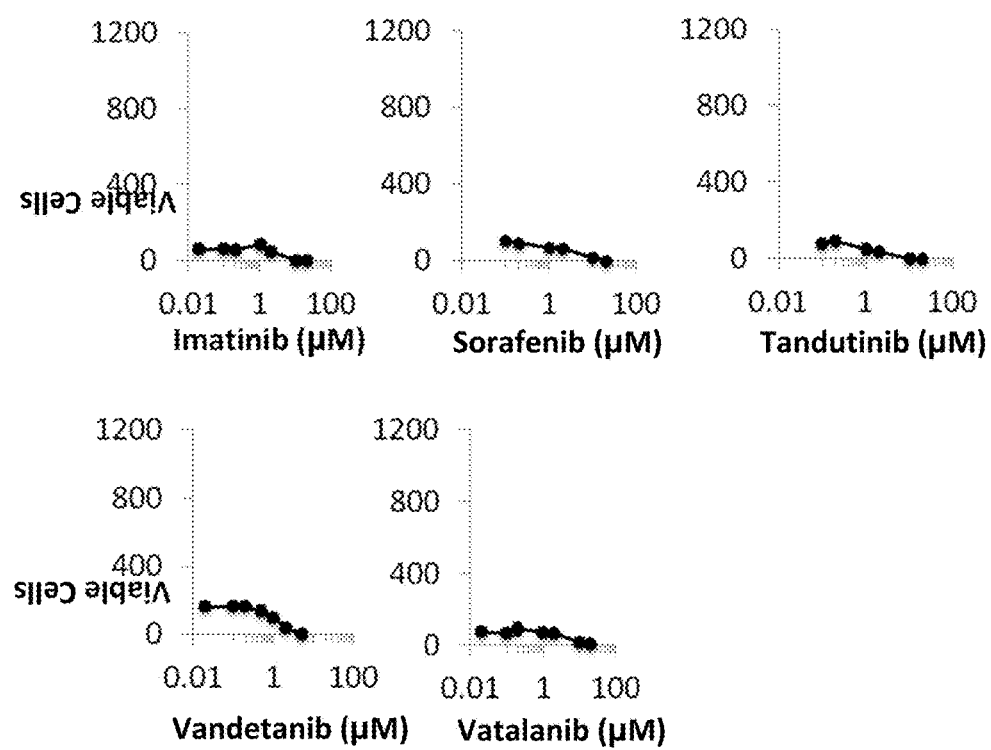
Figure 11:
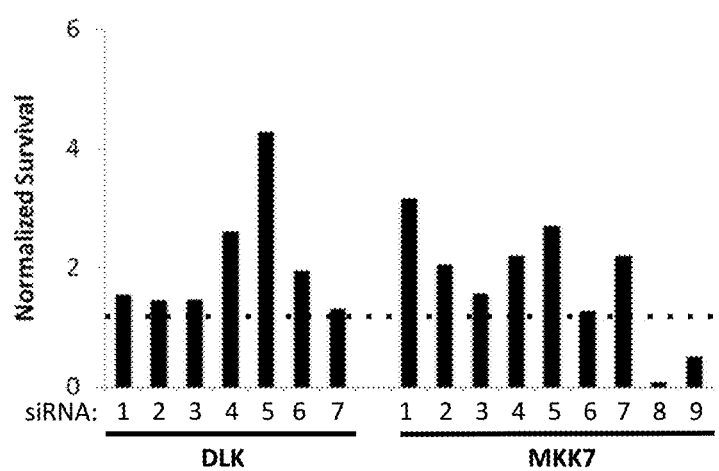
Figure 13:
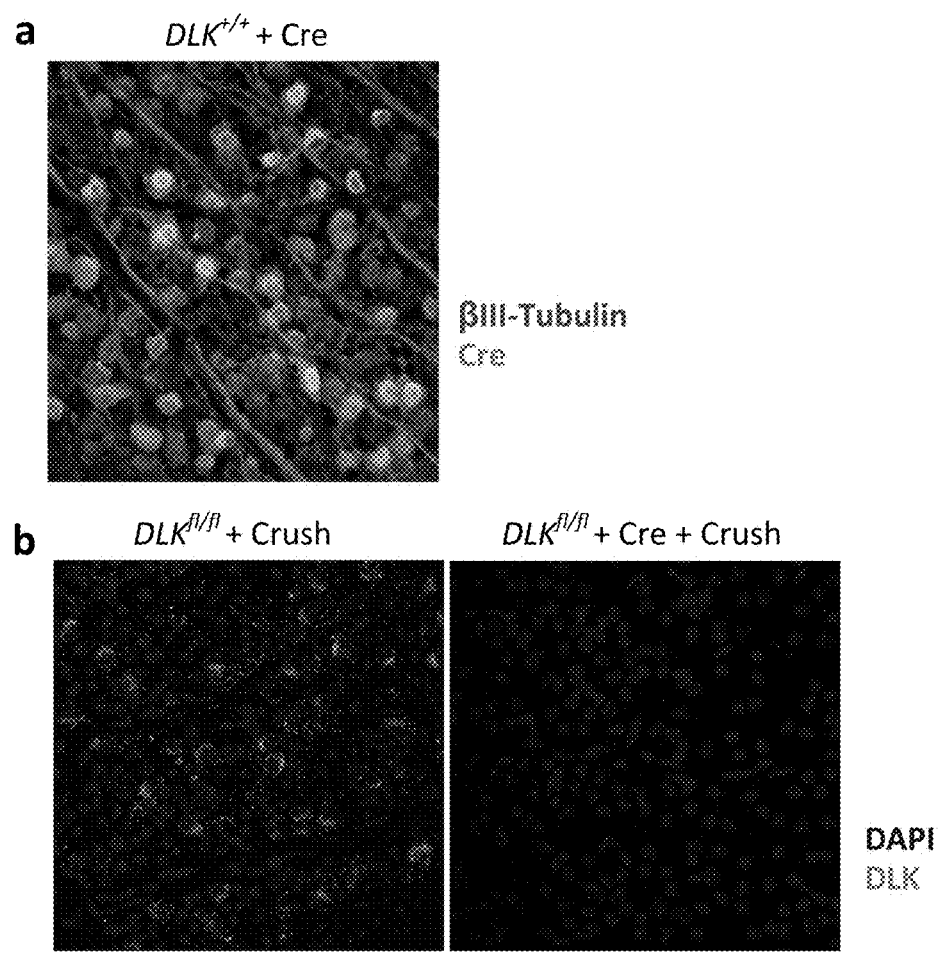
Figure 14:
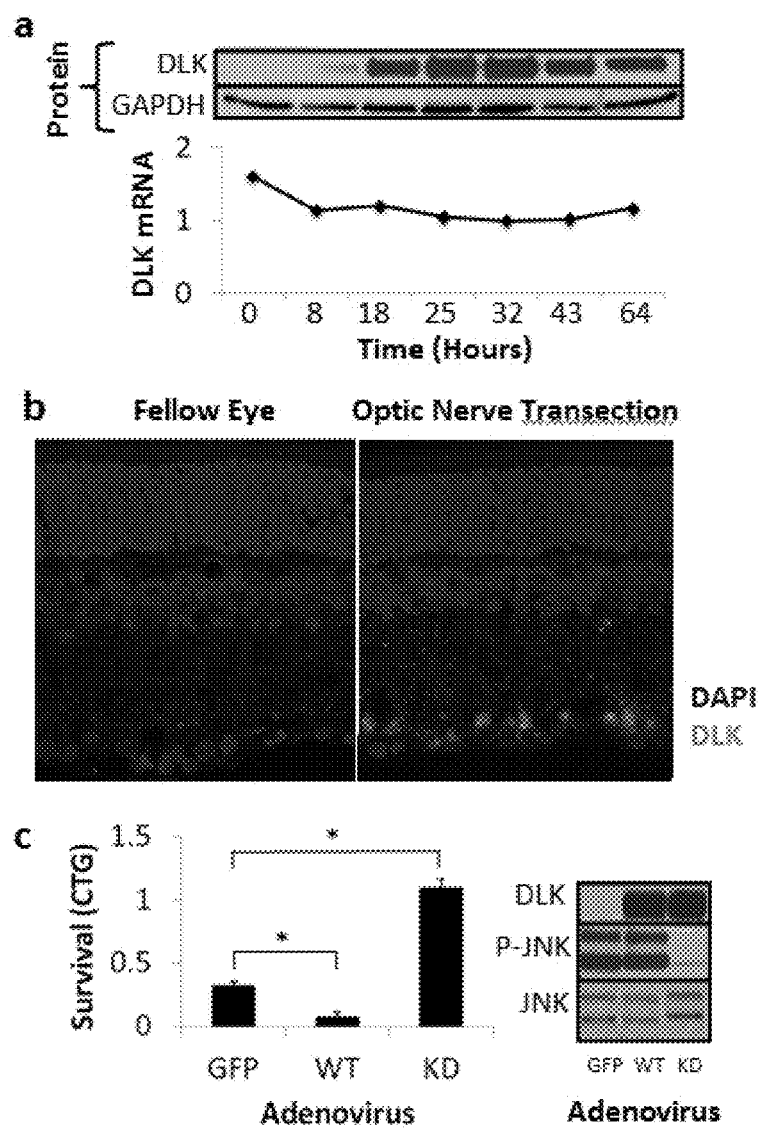
Figure 15:
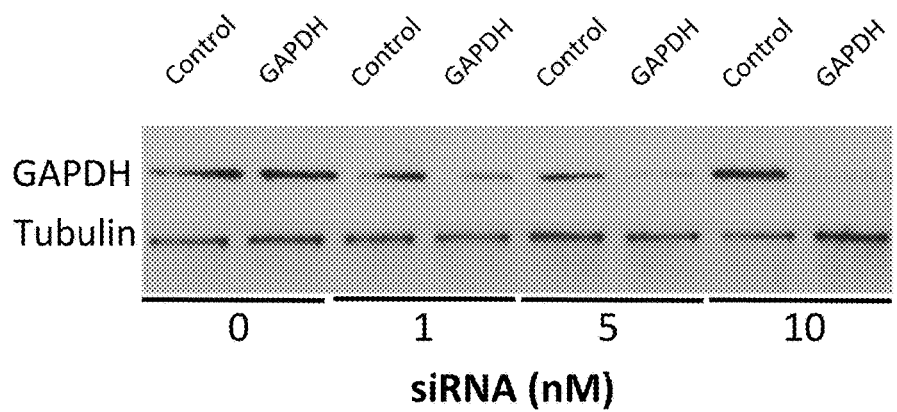
Figure 17:
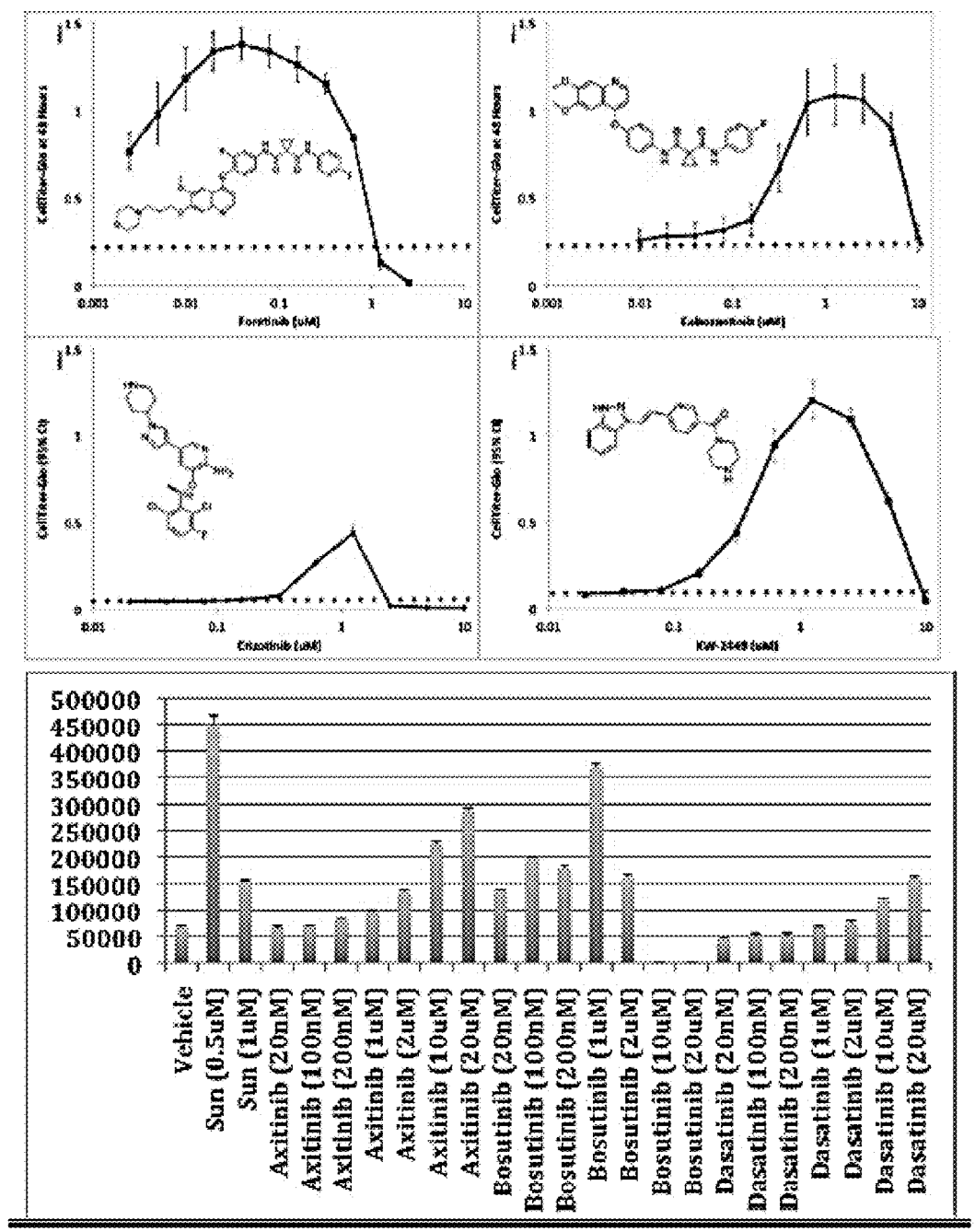
Figure 18:
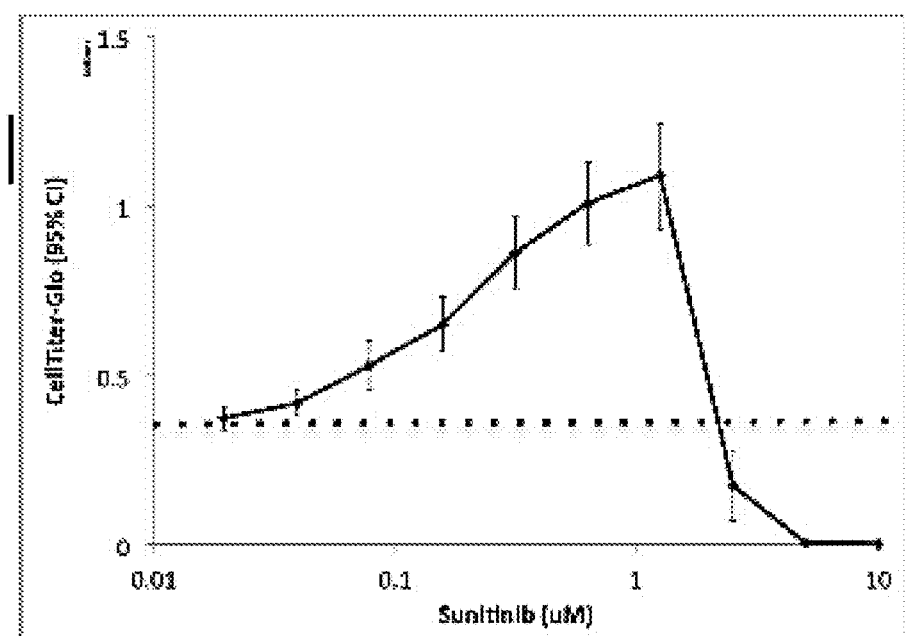
Figure 19:
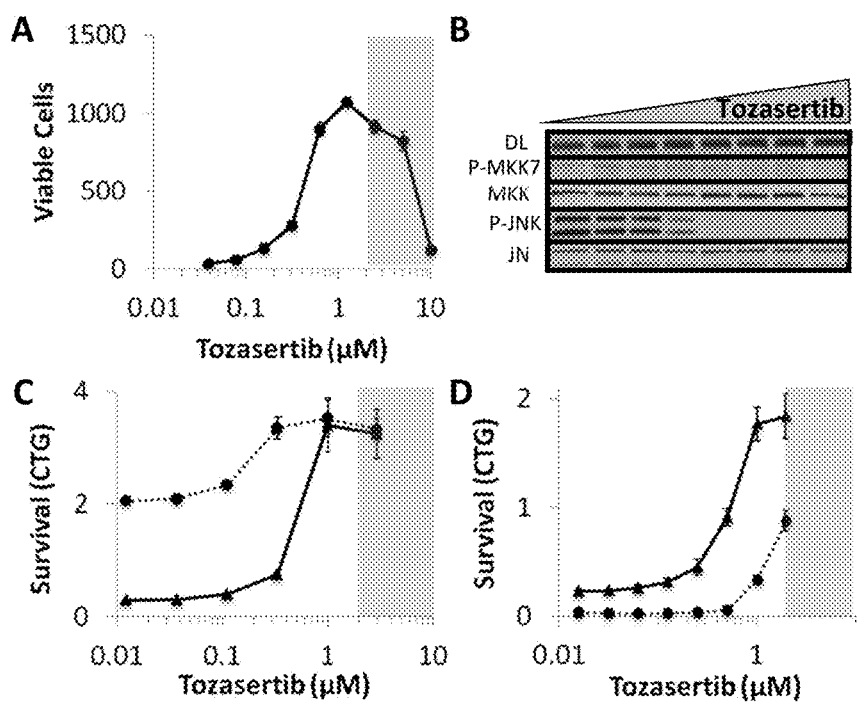
Figure 20:
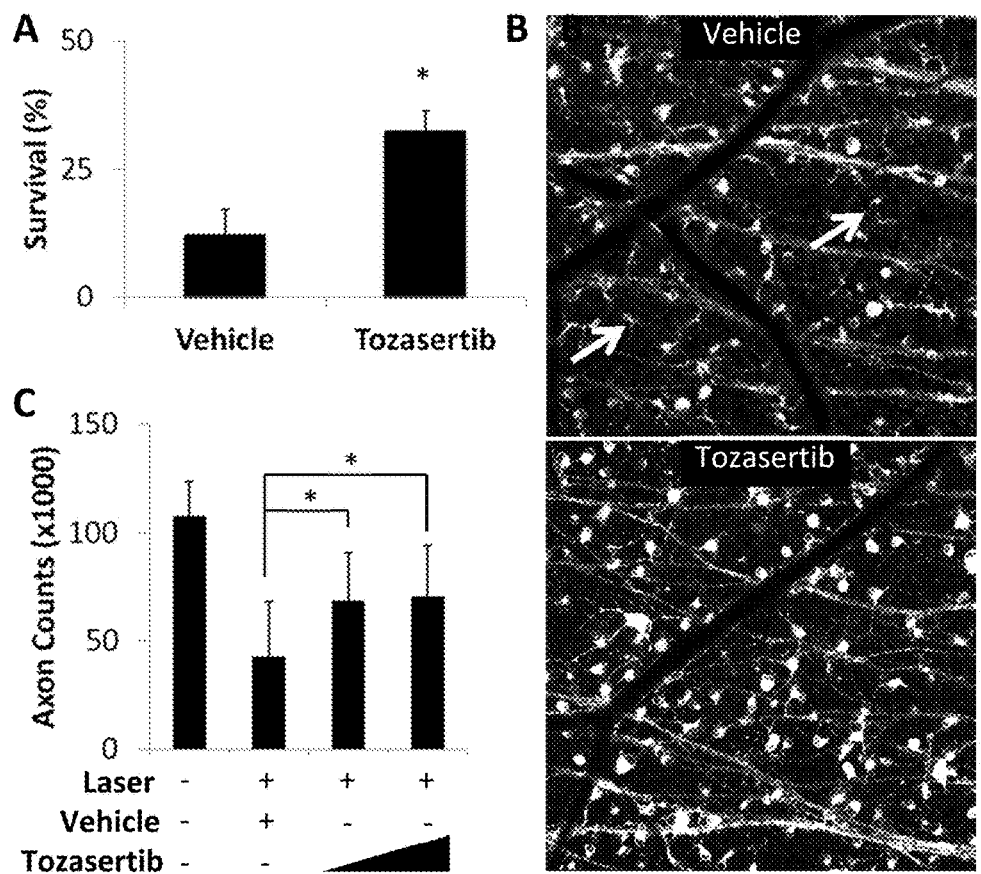

Having thus described the presently disclosed subject matter in general terms, reference will now be made to the accompanying Figures, which are not necessarily drawn to scale, and wherein:

FIGS. 1A to 1C show that sunitinib promotes retinal ganglion cell (RGC) survival in vitro and in vivo: (A) survival of immunopanned RGCs, treated with increasing doses of sunitinib, after 72 hours in culture; (B) survival of RGCs after optic nerve transection in rats pretreated with intravitreal drug-eluting slow-release particles or formulations, e.g., microspheres, containing vehicle (n=10), 440 ng sunitinib (n=6) or 300 ng SR8165 (n=10); and (C) optic nerve axon counts following laser-induced ocular hypertension in rats pretreated with intravitreal microspheres containing vehicle (n=29), 440 ng sunitinib (n=8) or 100 ng (n=24), 300 ng (n=26) or 600 ng (n=25) SR8165. Fellow eyes (n=157) shown for comparison. For each panel, representative images shown to the right. *$p<0.05$, #$p<0.005$; error bars, s.d.;

FIGS. 2A to 2C show that sunitinib inhibits RGC apoptosis in vitro: (A) immunopanned RGCs were cultured with increasing concentrations of sunitinib or the caspase inhibitor zVAD-FMK, for 24 hours. Caspase 3 activity was measured with a luminescent substrate (Caspase 3 Glo, Promega, Filchburg, Wis.); (B) purified mouse RGCs were cultured on coverslips for 48 hours in the presence or absence of sunitinib (0.5 μM). Nuclei were stained with DAPI, imaged and the number of pyknotic/fragmented quantified; and (C) bottom panel shows representative images;

FIGS. 3A to 3C show laser induced ocular hypertension: (A) schematic of rat glaucoma experiment; (B) mean intraocular pressure (TOP) increase 24 hours after the first administration of diode laser to the trabecular meshwork; and (C) IOP 24 hours after the first administration of diode laser, divided by treatment group;

FIGS. 4A to 4C show laser induced ocular hypertension: (A) schematic of rat glaucoma experiment; (B) mean IOP increase 24 hours after the first administration of diode laser to the trabecular meshwork. #$p<0.005$; Error bars show standard deviation; and (C) optic nerve axon counts following laser-induced ocular hypertension in rats pretreated with intravitreal microspheres containing vehicle (left) or tozaserti (right);

FIGS. 5A to 5C show the neuroprotection of SR8165, a sunitinib analog with greater efficacy in vitro: (A) structure of SR8165; (B) survival of immunopanned RGCs, treated with increasing doses of SR8165, after 72 hours in culture. The most efficacious doses of sunitinib are shown for comparison; and (C) structures of SU6656 and SR8020, an N-methyl derivative with impaired binding to the kinase ATP-binding pocket;

FIGS. 6A to 6E show the identification of dual-leucine zipper kinase (DLK) as a mediator of cell death in RGCs; (A) survival of immunopanned RGCs, comparing the sunitinib analog SU6656 (solid) to an N-methyl derivative, SR8020 (dashed), that has impaired binding to the kinase ATP-binding pocket; (B) histogram showing the normalized survival for control siRNAs (red), kinome library siRNAs (grey) and DLK siRNAs (arrows); (C) survival of immunopanned RGCs transfected with control (dashed) or DLK siRNA (solid); (D) patch-clamp recordings from RGCs maintained with DLK siRNA and/or sunitinib in response to depolarizing current (left) or glutamate iontophoresis (right); (E) survival of RGCs 10 days after optic nerve crush in $Dlk^{fl/fl}$ mice (n=3), $Dlk^{fl/fl}$ mice injected with AAV2-Cre (n=8) or $Dlk^{+/+}$ mice injected with AAV2-Cre (n=9), normalized to uninjured control mice (n=6). Representative images shown to the right. *$p<0.05$, #$p<0.005$; error bars, s.d.;

FIGS. 7A to 7F show the identification of DLK as a mediator of cell death in RGCs: (A) RGCs were transfected at the time of immunopanning with a fluorescently-labeled siRNA (siGLORed, Dharmacon) in the presence or absence of the magnetic nanoparticle, NeuroMag. After 24 hours, RGCs were imaged for viability (calcein-AM staining) and nuclear accumulation of siRNA; (B) histogram showing the normalized survival for control (black bars), kinome library (blue bars), DLK (red arrows) and MKK7 (green arrows) siRNAs. Oligonucleotides conferring survival more than 3 SD from the nontargeting siRNAs (dashed line) were considered neuroprotective (106 siRNA, 5.4%); (C) RGCs were transfected with DLK or a nontargeting control (NT) siRNA. mRNA (left) and protein (right) levels were quantified at 24 hours using RT-PCR and immunoblotting, respectively; (D) survival of immunopanned RGCs transfected with nontargeting (dashed) or DLK siRNA (solid); (E) expression of Brn3 in RGCs transfected with DLK or a nontargeting control (NT) siRNA; and (F) patch-clamp recordings from RGCs maintained with DLK siRNA in response to depolarizing current;

FIG. 8 shows that a genetic deletion of DLK protects RGCs from axonal injury-induced cell death in vivo. The survival of RGCs 10 days after optic nerve crush in Dlkfl/fl mice (n=3), Dlkfl/fl mice injected with AAV2-Cre (n=8) or Dlk+/+ mice injected with AAV2-Cre (n=9) is shown, normalized to uninjured control mice (n=6). Representative images shown to the right. *$p<0.05$, #$p<0.005$; Error bars show standard deviation;

FIG. 9 shows the lack of neuroprotective activity of kinase inhibitors targeting VEGFR2, c-Kit, FLT3 and PDGFRs. Survival of immunopanned RGCs, treated with increasing doses of the various kinase inhibitors, after 72 hours in culture;

FIGS. 10A and 10B show efficient and nontoxic siRNA delivery to primary RGCs: (A) RGCs were reverse transfected at the time of immunopanning with a fluorescently-labeled siRNA (siGLO-Red, Dharmacon) in the presence or absence of the magnetic nanoparticle, NeuroMag. After 24 hours, RGCs were imaged for viability (calcein-AM staining) and nuclear accumulation of siRNA; and (B) RGCs were reverse transfected with increasing doses of GAPDH or control siRNA (tubulin) in the presence of a fixed amount of NeuroMag and immunoblotted for GAPDH protein 24 hours later;

FIG. 11 shows secondary screening confirming the neuroprotective activity of DLK and MKK7 siRNAs. RGCs were immunopanned and transfected with an independent set of siRNAs not used in the initial screen. Candidate genes were considered confirmed if 75% of the secondary screening siRNA increased survival more than 3 SD above the control siRNAs;

FIGS. 12A and 12B show the knockdown of DLK mRNA and protein by DLK siRNA. RGCs were transfected with DLK or a nontargeting control (NT) siRNA. mRNA (A) and protein (B) levels were quantified at 24 hours using RT-PCR and immunoblotting, respectively;

FIGS. 13A and 13B show the AAV2-Cre-mediated deletion of Dlk in $Dlk^{fl/fl}$ mice: (A) $Dlk^{+/+}$ mice were intravitreally injected with AAV2-Cre. 7 days after infection, retinal flatmounts were stained for βIII-tubulin and Cre; and (B) three-month-old $Dlk^{+/+}$ or $Dlk^{fl/fl}$ mice were intravitreally injected with AAV2-Cre. 7 days later, eyes were subjected to optic nerve crush. 4 days after injury, retinal flatmounts were prepared and stained for DLK;

FIGS. 14A to 14C show that the DLK protein is upregulated in RGCs in response to injury: (A) levels of DLK protein (top) and mRNA (bottom), normalized to GAPDH, after various times in culture; (B) DLK immunofluorescence of retinal sections 72 hours after optic nerve transection in rats; and (C) survival, measured by CellTiter-Glo (CTG) luminescence, of immunopanned RGCs 48 hours after transduction with adenovirus (MOI 1000) expressing wildtype (WT) or kinase-dead (KD) DLK. Western blot showing the upregulation of DLK protein and corresponding response of the JNK pathway. *$p<0.05$; error bars, s.d.;

FIG. 15 shows the efficient delivery to primary RGCs. RGCs were reverse transfected with increasing doses of GAPDH or control siRNA in the presence of a fixed amount of NeuroMag and immunoblotted for GAPDH protein 24 hours later;

FIGS. 16A to 16D show DLK as a mediator of sunitinib's neuroprotective activity: (A) Western blot of the DLK pathway members in RGCs 4 hours after immunopanning in the presence of increasing doses of sunitinib; (B) survival of cultured RGCs 72 hours after transfection with DLK (solid) or control siRNA (dashed) in the presence of increasing doses of sunitinib; (C) survival of cultured RGCs 24 hours after transduction with DLK adenovirus (MOI 300) in the absence or presence of the sunitinib analog SR8165 (1 μM); and (D) survival of immunopanned RGCs, treated with increasing doses of the indicated DLK inhibitors, after 72 hours in culture. Bottom right panel shows the relationship between the biochemical $K_d$ (ability of the inhibitor to bind purified DLK) and the cellular $ED_{50}$. *$p<0.05$; error bars, s.d.;

FIGS. 17 and 18 show the RGC cell survival of murine purified RGCs demonstrating the neuroprotective activity of foretinib, cabozantinib, crizotinib, KW-2449, bosutinib, axitinib, and dasatinib with sunitinib as a positive control. Primary RGCs were cultured in neurotrophin-depleted media with increasing amounts of the indicated protein kinase inhibitor. Survival was measured 72 hours later with CellTiter-Glo luminescence. The dashed line indicates the survival of the vehicle-treated cells;

FIGS. 19A to 19D show that tozasertib inhibits DLK signaling in RGCs: (A) survival of immunopanned RGCs, treated with increasing doses of tozasertib, after 72 hours in culture. The shaded area indicates the toxic range for tozasertib; (B) Western blot of the DLK pathway members in RGCs 4 hours after immunopanning in the presence of 0, 0.03, 0.06, 0.125, 0.25, 0.5, 1 or 2 μM tozasertib; (C) survival of cultured RGCs 72 hours after transfection with DLK (dashed) or nontargeting siRNA (solid) in the presence of increasing doses of tozasertib; and (D) survival of cultured RGCs 48 hours after transduction with DLK expressing adenovirus in the presence of increasing doses of tozasertib. Error bars show standard deviation; and FIGS. 20A to 20C show that tozasertib promotes RGC survival in vivo: (A) survival of RGCs after optic nerve transection in rats pretreated with intravitreal drug-eluting slow-release particles or formulations, e.g., microspheres, containing vehicle (n=10) or 275 ng tozasertib (n=5); (B) optic nerve axon counts following laser induced ocular hypertension in rats pretreated with intravitreal drug-eluting microspheres containing vehicle (n=14), 82 ng (n=22) or 275 ng (n=21) tozasertib; and (C) graph of optic nerve axon counts following laser induced ocular hypertension in rats pretreated with intravitreal drug-eluting microspheres containing vehicle or tozasertib. Fellow eyes (n=57) shown for comparison. *p<0.05; Error bars show standard deviation.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Compounds, Compositions, and Methods for Treating Neurodegenerative Disorders Glaucoma is a major cause of visual loss and blindness in elderly Americans and throughout the world. One approach for treating glaucoma and other optic nerve diseases, as well as other neurodegenerative diseases, disorders, or conditions is through neuroprotective agents that promote the survival of neurons or a portion thereof (e.g., the neuron cell body, an axon, or a dendrite).

It previously has been shown that protein kinase inhibitors identified through a high content screen of libraries of small molecule compounds can promote the survival and/or neurite outgrowth of retinal ganglion cells (RGCs). See, for example, International PCT Patent Application Publication Nos., WO2010/017541, to Zack et al., published Feb. 11, 2010, and WO2011/119777 to Zack et al., published Sep. 29, 2011, each of which is incorporated by reference in their entirety. RGCs are cells in the retina that die in glaucoma and whose loss leads to vision loss. Accordingly, based on the activity of the presently disclosed compounds on RGCs, the presently disclosed compounds can be used for treating glaucoma, retinitis pigmentosa, and age-related macular degeneration, and/or other optic nerve diseases. Further, based on their activity on other neurons, e.g., hippocampal cell cultures, the presently disclosed compounds can be used to treat other neurodegenerative diseases in which there is a decreased function and/or loss of neurons.

Current therapies for glaucoma all act by lowering intraocular pressure (TOP). Pressure reduction, however, can be difficult to achieve, and even with significant pressure lowering, RGC loss can continue. Efforts have therefore been made to develop neuroprotective agents that would complement IOP-lowering by directly inhibiting the RGC cell death process, though no neuroprotective agent is yet in clinical use (Danesh-Meyer and Levin, 2009).

A. Methods of Treatment

In some embodiments, the presently disclosed subject matter provides a method for treating or preventing a neurodegenerative disease, disorder, or condition in a subject in need thereof, the method comprising administering to the subject a therapeutically effective amount of a compound of Formula (I), or a pharmaceutically acceptable salt, hydrate, or prodrug thereof, thereby treating or preventing the neurodegenerative disease, disorder, or condition:

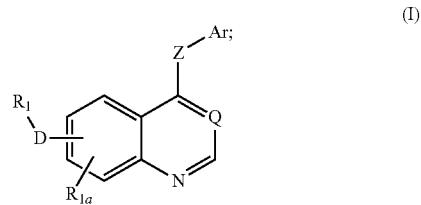

(I)

wherein:

D is selected from the group consisting of O, $S(O)_{0-2}$, and $N_{R1b}$;

$R_{1a}$ is selected from the group consisting of H, substituted or unsubstituted alkyl, halogen, $OR_{1b}$, $NO_2$, $NR_{1b}R_{1c}$;

wherein: $R_{1b}$ and $R_{1c}$ are each independently selected from the group consisting of H or substituted or unsubstituted alkyl, aryl, arylalkyl, heterocyclyl, and heterocyclylalkyl; and wherein $R_{1b}$ and $R_{1c}$ when taken together with a common nitrogen to which they are attached, form an optionally substituted five- to seven-membered heterocyclyl, the optionally substituted five- to seven-membered heterocyclyl optionally containing at least one additional annular heteroatom selected from N, O, S, and P;

$R_1$ is selected from the group consisting of H, substituted or unsubstituted alkyl, aryl, arylalkyl, heterocyclyl, and heterocyclylalkyl, or $R^{50}$ as defined in paragraphs [0036-0046] of U.S. Patent Application Publication No. US20070054928;

Q is selected from the group consisting of $CR_{2a}$ or N, wherein $R_{2a}$ is selected from the group consisting of H, alkyl, and cyano;

Z is selected from the group consisting of O, $NR_{1b}$, and $S(O)_{0-2}$; and

Ar is substituted aryl or substituted heteroaryl, wherein at least one substituent group on Ar comprises the group B-L-T, as defined in paragraphs [0033-0036] of U.S. Patent Application Publication No. US20070054928.

Representative compounds of Formula (I) suitable for use with the presently disclosed subject matter are disclosed in U.S. Patent Application Publication Nos. US20070054928, US20070225307, US20070244116, US20090105299, US20090170896, US20110077233, and US20120022065 and U.S. Pat. Nos. 7,579,473, 8,067,436, and 8,178,532, each of which is incorporated herein by reference in its entirety. In particular embodiments, the compound of Formula (I) is a compound disclosed in paragraphs [0033-0165], including those compounds disclosed in Table 1 and Table 2, of U.S. Patent Application Publication No. US20070054928. In yet more particular embodiments, the compound of Formula (I) comprises a compound disclosed in Table 2, of U.S. Patent Application Publication No. US20070054928.

In some embodiments, the compound of Formula (I) is a compound of formula A-B—C as defined in paragraphs [0095-0165] of U.S. Patent Application Publication No. US20070054928. In more particular embodiments, the compound of Formula (I) is a compound of Formula (XI) as disclosed in paragraphs [0109-0117] of U.S. Patent Application Publication No. US20070054928:

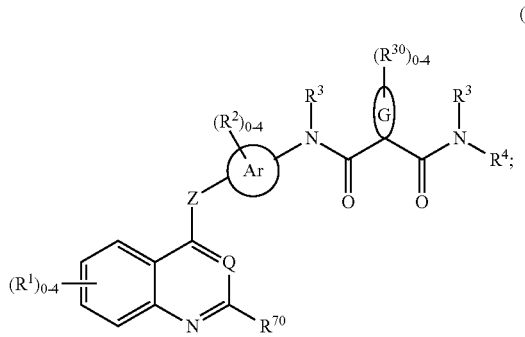
(XI)

wherein: $R^1$, $R^2$, $R^3$, $R^4$, $R^{30}$, $R^{70}$, Q, Z, Ar, and G are defined therein.

In yet more particular embodiments, the compound of Formula (I) is a compound of Formula (XIIIa) or (XIIIb) as disclosed in paragraphs [0118-0126] of U.S. Patent Application Publication No. US20070054928:

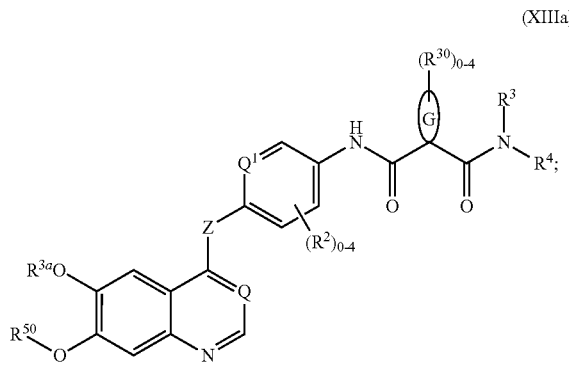
(XIIIa)

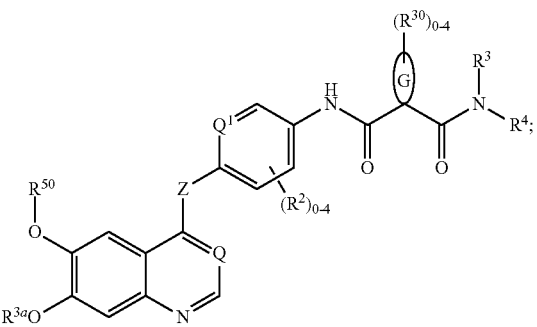
(XIIIb)

wherein $R^2$, $R^3$, $R^4$, $R^{3a}$, $R^{30}$, $R^{50}$, Q, $Q^1$, and G are defined therein.

In some embodiments, the compound of Formula (I) is a compound of Formula (XIVa) or Formula (XIVb), as disclosed in paragraphs [0126-0165] of U.S. Patent Application Publication No. US20070054928:

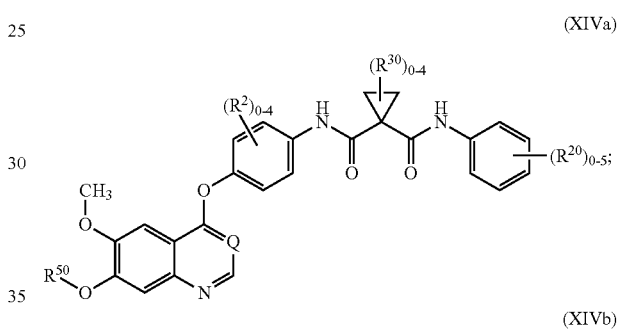
(XIVa)

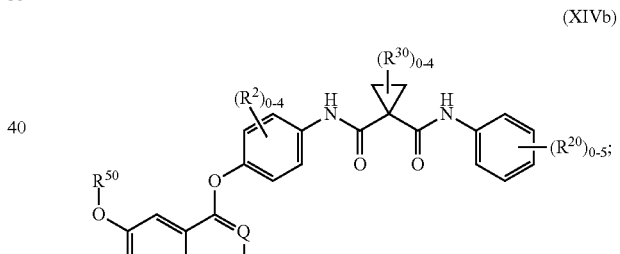
(XIVb)

wherein: $R^{50}$, Q, $R^2$, $R^{30}$, and $R^{20}$ are defined therein.

In particular embodiments, the compound of Formula (XIVa) is foretinib (also referred to as XL-880 or GSK1363069):

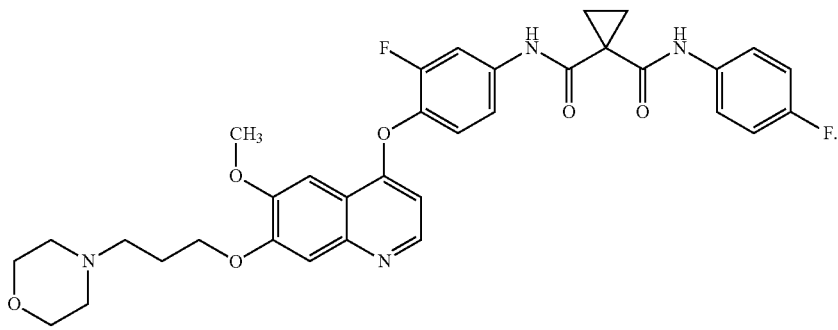 [SMILES: COc1cc2c(Oc3ccc(NC(=O)C4(C(=O)Nc5ccc(F)cc5)CC4)cc3F)ccnc2cc1OCCCN1CCOCC1]

In some embodiments, the compound of Formula (XIVb) is selected from the group consisting of:

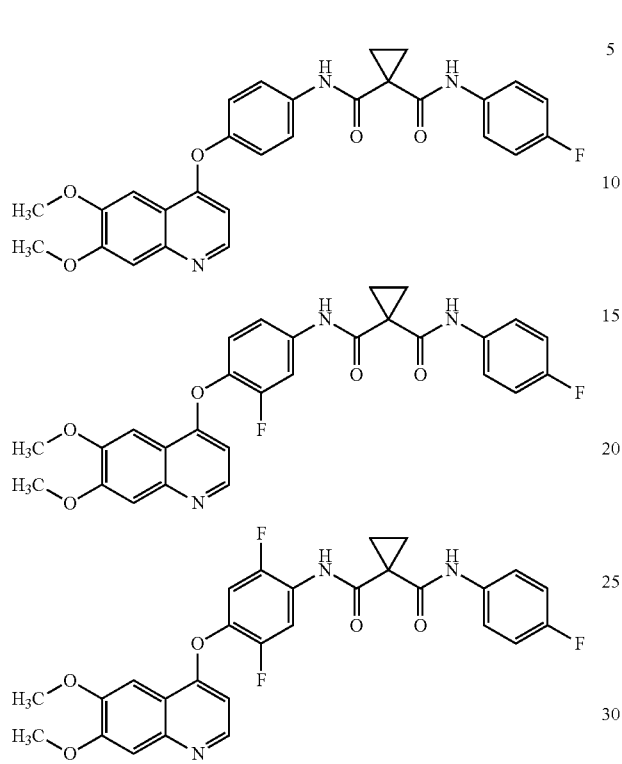

In particular embodiments, the compound of Formula (XIVb) is cabozantinib (also referred to as XL-184):

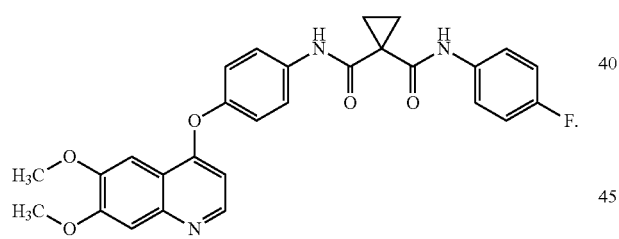

In yet other embodiments, the compound is crizotinib, or a related compound disclosed in U.S. Pat. Nos. 7,230,098, 7,825,137, and 7,858,643, each of which is incorporated herein in its entirety:

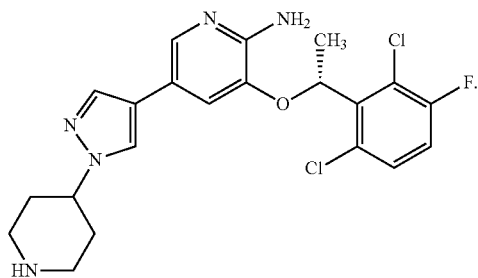 [SMILES: C[C@@H](Oc1cc(-c2cnn(C3CCNCC3)c2)cnc1N)c1c(Cl)ccc(F)c1Cl]

In some embodiments, the compound is KW-2449:

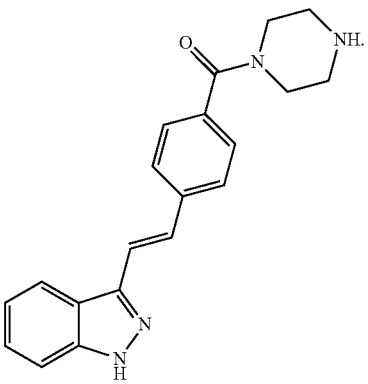 [SMILES: O=C(c1ccc(/C=C/c2n[nH]c3ccccc23)cc1)N1CCNCC1]

In yet other embodiments, the compound is bosutinib:

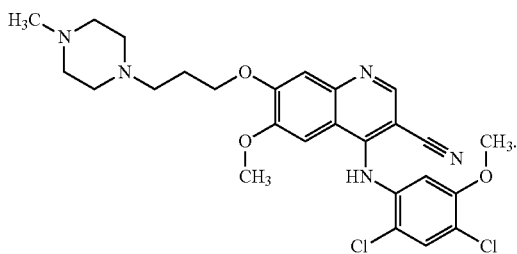 [SMILES: COc1cc(Nc2c(C#N)cnc3cc(OCCCN4CCN(C)CC4)c(OC)cc23)c(Cl)cc1Cl]

In yet other embodiments, the compound is axitinib:

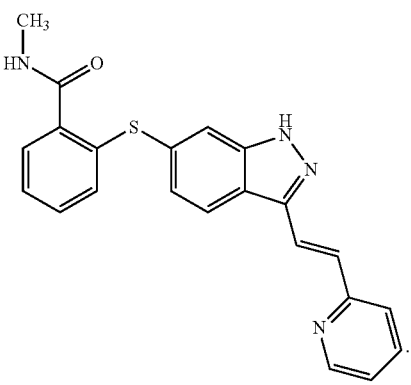 [SMILES: CNC(=O)c1ccccc1Sc1ccc2c(/C=C/c3ccccn3)n[nH]c2c1]

In yet further embodiments, the kinase modulator is dasatinib, also referred to as BMS-354825 or Sprycel®, or a related compound disclosed in U.S. Pat. Nos. 6,596,746, 7,125,875, 7,153,856, and 7,491,725, each of which is incorporated herein by reference in its entirety:

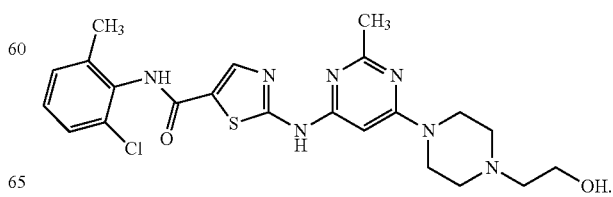

Accordingly, in some embodiments, the presently disclosed subject matter relates to compounds, and methods of use thereof, which can promote the survival and/or neurite outgrowth of retinal ganglion cells (RGCs) and/or photoreceptor cells. In some embodiments, a compound of Formula (I), or other compounds disclosed herein, or a pharmaceutically acceptable salt thereof, can prevent the death of one or more damaged neuronal cells. In other embodiments, a compound of Formula (I), or other compounds disclosed herein, can be used to promote the growth or regeneration of all or part of a neuronal cell, including, but not limited to, the growth of a neurite, such as an axon, a dendrite, and the like.

As used herein, a "neuron or portion thereof" can consist of or be a portion of a neuron selected from the group consisting of a cerebellar granule neuron, a dorsal root ganglion neuron, a cortical neuron, a sympathetic neuron, and a hippocampal neuron. More particularly, the term "neuron" as used herein denotes nervous system cells that include a central cell body or soma, and two types of extensions or projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column) Certain specific examples of neuron types that may be subject to treatment according to the presently disclosed subject matter include cerebellar granule neurons, dorsal root ganglion neurons, and cortical neurons. Further, as used herein, the term "neurite" means a projection from the cell body of a neuron including, e.g., an axon or a dendrite.

Without wishing to be bound to any one particular theory, it is believed that the presently disclosed compounds can modulate: (i) the activity or expression of a target protein in the neuron or portion thereof; (ii) a process in the neuron or portion thereof; or (iii) a biological pathway associated with a neurodegenerative disease, disorder, or condition. In particular embodiments, the presently disclosed compounds inhibit one or more protein kinases involved in a biological pathway associated with a neurodegenerative disease, disorder, or condition. As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a neurodegenerative disease, disorder, or condition. It will be appreciated that, although not precluded, treating a disease, disorder or condition does not require that the disease, disorder, condition or symptoms associated therewith be completely eliminated.

In some embodiments, the neuron or portion thereof can be present in a subject, such as a human subject. The subject can, for example, have or be at risk of developing a disease, disorder, or condition selected from the group consisting of (i) a disease, disorder, or condition of the nervous system; (ii) a condition of the nervous system that is secondary to a disease, disorder, or condition, or a therapy having a primary effect outside of the nervous system; (iii) an injury to the nervous system, such as, for example, an injury caused by physical, mechanical, or chemical trauma; (iv) pain; (v) ocular-related neurodegeneration; (vi) memory loss; and (vii) a psychiatric disorder.

Accordingly, in some embodiments, a compound of Formula (I) can be used to treat or prevent a neurodegenerative disease, disorder, or condition. As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound of Formula (I), or other compounds disclosed herein, or another agent, e.g., a peptide, nucleic acid molecule, or other small molecule compound administered in combination with a compound of Formula (I), or other compounds disclosed herein. More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to contacting a neuron or portion thereof with a compound of Formula (I), or other compounds disclosed herein. This term includes administration of the presently disclosed compounds to a subject in which the neuron or portion thereof is present, as well as introducing the presently disclosed compounds into a medium in which a neuron or portion thereof is cultured.

By "contacting" a cell, it is meant any action that results in at least one molecule of one of the presently disclosed compounds physically contacting at least one cell. It thus may comprise exposing the cell(s) to the compound in an amount sufficient to result in contact of at least one molecule of compound with at least one cell. The method can be practiced in vitro or ex vivo, by introducing, and preferably mixing, the compound and cells in a controlled environment, such as a culture dish or tube. The method can be practiced in vivo, in which case contacting means exposing at least one cell in a subject to at least one molecule of compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s).

By "neurodegenerative disease, disorder, or condition" is meant a disease, disorder, or condition (including a neuropathy) associated with degeneration or dysfunction of neurons or other neural cells, such as retinal ganglion cells or photoreceptor cells. A neurodegenerative disease, disorder, or condition can be any disease, disorder, or condition in which decreased function or dysfunction of neurons, or loss or neurons or other neural cells, can occur. Particular targets associated with neurodegenerative diseases, disorders, or conditions are disclosed in International PCT Patent Application Publication No. WO2011/050192 to Lewcock et al., published Apr. 28, 2011, which is incorporated herein by reference in its entirety. As used herein, the term "disorder" in general refers to any condition that would benefit from treatment with a compound of Formula (I), including any disease, disorder, or condition that can be treated by an effective amount of a compound of Formula (I), or other compounds disclosed herein, or a pharmaceutically acceptable salt thereof.

Such diseases, disorders, or conditions include, but are not limited to, glaucoma, retinitis pigmentosa, and age-related macular degeneration, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS dementia complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Examples of ocular-related neurodegeneration include, but are not limited to, glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis.

Non-limiting examples of different types of glaucoma that can be prevented or treated according to the presently disclosed subject matter include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy. In certain embodiments, the neurodegenerative disease, disorder, or condition is a disease, disorder, or condition that is not associated with excessive angiogenesis, for example, a glaucoma that is not neovascular glaucoma.

Examples of conditions of the nervous system that are secondary to a disease, disorder, condition, or therapy having a primary effect outside of the nervous system include, but are not limited to, peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, syphilis, systemic lupus erythematosus, and amyloidosis.

Examples of pain include, but are not limited to, chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, a torn ligament, and diabetes.

Examples of injuries to the nervous system caused by physical, mechanical, or chemical trauma include, but are not limited to, nerve damage caused by exposure to toxic compounds, heavy metals (e.g., lead, arsenic, and mercury), industrial solvents, drugs, chemotherapeutic agents, dapsone, HIV medications (e.g., zidovudine, didanosine, stavudine, zalcitabine, ritonavir, and amprenavir), cholesterol lowering drugs (e.g., lovastatin, indapamide, and gemfibrozil), heart or blood pressure medications (e.g., amiodarone, hydralazine, perhexiline), and metronidazole.

Further examples also include burn, wound, surgery, accidents, ischemia, prolonged exposure to cold temperature (e.g., frost bite), stroke, intracranial hemorrhage, and cerebral hemorrhage. More particularly, traumatic injury or other damage to neuronal cells (e.g., trauma due to accident, blunt-force injury, gunshot injury, spinal cord injury, ischemic conditions of the nervous system such as stroke, cell damage due to aging or oxidative stress, and the like) also is intended to be included within the language "neurodegenerative disease, disorder, or condition." In such embodiments, the presently disclosed methods can be used to treat neuronal damage due to traumatic injury or stroke by preventing death of damaged neuronal cells and/or by promoting or stimulating neurite growth from damaged neuronal cells.

Examples of psychiatric disorders include, but are not limited to, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, e.g., optic crush experiments, and the like).

In particular embodiments, the subject is suffering from or susceptible to a neurodegenerative disease, disorder, or condition, such as glaucoma, e.g., a subject diagnosed as suffering from or susceptible to a neurodegenerative disease, disorder, or condition. In other embodiments, the subject has been identified (e.g., diagnosed) as suffering from or susceptible to a neurodegenerative disease, disorder, or condition (including traumatic injury) in which neuronal cell loss is implicated, or in which damage to neurites is involved, and for which treatment or prophylaxis is desired.

In certain embodiments, the subject is not suffering, or has not been diagnosed as suffering, from cancer. In certain embodiments, the subject is not suffering, or has not been diagnosed as suffering, from a disorder related to excess angiogenesis. In certain embodiments in which a cell is contacted with a compound of Formula (I), or a pharmaceutically acceptable salt thereof, the cell is not a neoplastic cell. In certain embodiments of the above aspects, the cell is a mammalian cell, more preferably a human cell.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% decrease in cell loss or loss of function relative to cell survival or cell function measured in absence of the tested compound, i.e., a control sample, in an assay. In other embodiments, the compounds and amounts for use in the presently disclosed therapeutic methods produce at least about 10% to 15% increase in neuron count, neuron function, neurite count, neurite total length, or neurite average length relative to absence of the tested compound in an assay.

In any of the above-described methods, the administering of a compound of Formula (I) can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8, 9, or 10) symptoms of a disease, disorder, or condition of the nervous system; a condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a subject that is not administered the one or more of the agents described herein.

Non-limiting examples of such symptoms include, but are not limited to, tremors, slowness of movement, ataxia, loss of balance, depression, decreased cognitive function, short-term memory loss, long-term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

In any of the above-described methods, the administering of a compound of Formula (I) results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition of the nervous system; condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a control population of subjects that are not administered a compound of Formula (I).

The administration of one or more agent as described herein may result in at least about a 10%, 15%, 20%, 25%, 30%, 35%, 40%, 45%, 50%, 55%, 60%, 65%, 70%, 75%, 80%, 85%, 90%, 95%, or even 100% decrease in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein.

In some embodiments, the presently disclosed methods include preventing or inhibiting neuron or axon degeneration. The phrases "preventing axon degeneration," "preventing neuron degeneration," "inhibiting axon degeneration," or "inhibiting neuron degeneration" as used herein include: (i) the ability to inhibit or prevent axon or neuron degeneration in patients newly diagnosed as having a neurodegenerative disease or at risk of developing a new neurodegenerative disease; and (ii) the ability to inhibit or prevent further axon or neuron degeneration in patients who are already suffering from, or have symptoms of, a neurodegenerative disease. Preventing axon or neuron degeneration includes decreasing or inhibiting axon or neuron degeneration, which may be characterized by complete or partial inhibition of neuron or axon degeneration. Such prevention or inhibition can be assessed, for example, by analysis of neurological function. Further, the phrases "preventing neuron degeneration" and "inhibiting neuron degeneration" include such inhibition with respect to the entire neuron or a portion thereof, such as the neuron cell body, axons, and dendrites.

The above-listed terms also include in vitro and ex vivo methods. For example, in certain embodiments, the presently disclosed methods are applicable to cell culture techniques wherein it is desirable to prevent neuronal cell death or loss of neuronal function. In vitro neuronal culture systems have proved to be fundamental and indispensable tools for the study of neural development, as well as the identification of neurotrophic factors, such as nerve growth factor (NGF), ciliary trophic factors (CNTF), and brain derived neurotrophic factor (BDNF). One use of certain embodiments of the presently disclosed methods is in cultures of neuronal cells, such as in the use of such cultures for the generation of new neurons and glia. In such embodiments, the cultured cells can be contacted with a compound of Formula (I) to prevent neuronal cell death or loss of neuronal function. In an exemplary embodiment, the subject method can be used to culture, for example, sensory neurons or, alternatively, motoneurons. Such neuronal cultures can be used as convenient assay systems, as well as sources of implantable cells for therapeutic treatments.

In other examples, the neuron or portion thereof treated according to the presently disclosed methods is ex vivo or in vitro. Accordingly, the presently disclosed compounds can be useful as components of culture media for use in culturing nerve cells in vitro. More particularly, in certain embodiments, the presently disclosed methods can be used to improve the survival or integration of transplanted neuronal cells into a host subject (e.g., through a nerve graft or nerve transplant). Thus, for example, a subject receiving a transplant of neuronal cells can be treated (before, during, or after the transplantation procedure) with compounds according to the presently disclosed methods, to prevent cell death of the transplanted cells (or host cells that may be perturbed during the transplantation procedure), and/or to promote the growth of neurites in the transplanted cells or the host neuronal cells, and thereby promote integration of the transplanted cells into the host nervous system.

The presently disclosed subject matter further provides methods of modulating the growth, cell size, and/or proliferation of a neuron (e.g., cerebellar granule neuron, a dorsal root ganglion neuron, a cortical neuron, or a sympathetic neuron) by contacting a neuron with a compound of Formula (I).

In an embodiment, the presently disclosed subject matter provides a method for promoting or stimulating RGC or photoreceptor cell survival by contacting the RGC or photoreceptor cell with a compound of Formula (I). The method comprises contacting a RGC or photoreceptor cell with at least one compound of Formula (I) in an amount sufficient to promote RGC or photoreceptor cell survival. In other words, a method is disclosed that can be used to inhibit or prevent RGC or photoreceptor cell death. The method comprises contacting a RGC or photoreceptor cell with at least one compound of Formula (I) in an amount sufficient to inhibit RGC or photoreceptor cell death. These methods may be performed in vitro, in vivo, or ex vivo. These methods may promote RGC survival, photoreceptor cell survival, or survival of both types of cells simultaneously.

It is shown herein below that DLK is a mediator of cell death in RGCs. It is also shown that certain compounds of Formula (I) promote RGC survival by inhibiting the DLK pathway. Therefore, in a particular embodiment, a compound of Formula (I) inhibits the DLK pathway. This inhibition results in the promotion or stimulation of RGC survival or the inhibition of RGC death.

Further, it is shown that the DLK protein is undetectable in uninjured RGCs both in vitro and in vivo, but that there is a significant upregulation of DLK protein in injured RGCs. Therefore, in another embodiment, the presently disclosed subject matter provides a method for using the DLK protein as a biomarker for RGC or photoreceptor cell injury. In particular, the presently disclosed subject matter provides a method for identifying injury to an RGC or a photoreceptor cell, the method comprising measuring levels of dual-leucine zipper kinase (DLK) protein in the RGC or photoreceptor cell; and comparing the levels of DLK protein in the RGC or photoreceptor cell to the levels of DLK protein in a control RGC or photoreceptor cell; wherein a significant difference between the levels of DLK protein in the RGC or photoreceptor cell and the levels of DLK protein in the control RGC or photoreceptor cell is indicative of injury to the RGC or photoreceptor cell.

Further, it is thought that LZK, another member of the serine/threonine protein kinase family, and a protein that also is comprised of a leucine-zipper motif, also can be inhibited by certain compounds of Formula (I) to promote RGC or photoreceptor cell survival. Therefore, in another embodiment, the presently disclosed subject matter provides a method for using the LZK protein as a biomarker for RGC or photoreceptor cell injury. In particular, the presently disclosed subject matter provides a method for identifying injury to an RGC or a photoreceptor cell, the method comprising measuring levels of LZK protein in the RGC or photoreceptor cell; and comparing the levels of LZK protein in the RGC or photoreceptor cell to the levels of LZK protein in a control RGC or photoreceptor cell; wherein a significant difference between the levels of LZK protein in the RGC or photoreceptor cell and the levels of LZK protein in the control RGC or photoreceptor cell is indicative of injury to the RGC or photoreceptor cell.

As used herein, the term "control RGC or photoreceptor cell" means an RGC or photoreceptor cell that is known to be uninjured. In these methods, levels of DLK and/or LZK protein in the potentially injured RGC or photoreceptor cell will correlate with the levels of DLK and/or LZK protein in a RGC or photoreceptor cell that has been injured if the RGC or photoreceptor cell in question has also been injured. Levels of DLK and/or LZK protein in a RGC or photoreceptor cell in question will correlate with the levels measured in a control RGC or photoreceptor cell if the RGC or photoreceptor cell in question has not been injured.

In another embodiment, the presently disclosed subject matter provides a method for identifying injury to an RGC or a photoreceptor cell in a subject, the method comprising: (a) obtaining a sample from a subject; (b) measuring levels of dual-leucine zipper kinase (DLK) protein and/or leucine zipper-bearing kinase (LZK) protein in the sample; and (c) comparing the levels of DLK protein and/or LZK protein in the sample with the levels of DLK protein and/or LZK protein in a control sample; wherein a significant difference between the levels DLK protein and/or LZK protein in the sample and the levels of DLK protein and/or LZK protein in the control sample is indicative of injury to a RGC or photoreceptor cell in the subject.

As used herein, the term "sample" refers to any sampling of cells, tissues, or bodily fluids in which expression of a biomarker of interest can be detected. The sample may be a part of a subject in vivo or ex vivo. In particular embodiments, the sample for use in the present methods is selected from the group consisting of the vitreous, the aqueous of the eye, and serum.

As used herein, the term "control sample", "corresponding control", or "appropriate control" means any control or standard familiar to one of ordinary skill in the art useful for comparison purposes. For example, where the sample for use in the present methods is the vitreous, the aqueous of the eye, or serum, appropriate corresponding control samples would be the vitreous, the aqueous of the eye, or serum taken from a subject or subjects that do not have injury to a RGC or photoreceptor cell.

As used herein, the term "level" or "level of expression" of a protein or biomarker refers to the amount of a given protein or biomarker that is detected. Levels of proteins or biomarkers can be detected at the transcriptional level, the translational level, and the post-translational level, for example.

As used herein, the terms "significantly different" or "significant difference" mean a level of expression of a biomarker in a sample that is higher or lower than the level of expression of the biomarker in a control sample by at least 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold or more.

Those of skill in the art are well aware of, and fully capable of selecting and executing, appropriate assays for measuring levels of DLK or LZK protein. Examples include, but are not limited to, immunohistochemical assays, Western blot analyses, ELISAs, and the like. Depending on the assay used, the method to determine if a RGC or photoreceptor cell has been injured may be a simple +/− assay in which detectable amounts of DLK or LZK protein means that the RGC or photoreceptor cell has been injured and undetectable amounts means that the RGC has not been injured. In other assays, the relative amounts of DLK or LZK protein may be compared to determine if there is an increase or decrease in protein levels.

B. Pharmaceutical Compositions

The presently disclosed pharmaceutical compositions and formulations include pharmaceutical compositions of compounds of Formula (I), or other compounds disclosed herein, alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of a compound of Formula (I) is selected from the group consisting of HCl, a sulfonate, a sulfate, phosphate, a malonate, a succinate, a fumarate, a maleate, a tartrate, a 3-sulfopropanoic acid salt, and a citrate. Suitable salts of the presently disclosed compounds are disclosed in International PCT Patent Application Publication No. WO2004/000833 to Charrier et al., published Dec. 31, 2003, which is incorporated herein by reference in its entirety.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

C. Combination Therapies

In certain embodiments, the presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formula (I), or other compounds disclosed herein. Alternatively, these agents may be part of a single dosage form, mixed together with the compound of Formula (I), or other compounds disclosed herein, in a single composition.

By "in combination with" is meant the administration of a compound of Formula (I), or other compounds disclosed herein, with one or more therapeutic agents either simultaneously, sequentially, or a combination thereof. Therefore, a cell or a subject administered a combination of a compound of Formula (I), or other compounds disclosed herein, can receive a compound of Formula (I), or other compounds disclosed herein, and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I), or other compounds disclosed herein, and one or more therapeutic agents are administered simultaneously, they can be administered to the cell or administered to the subject as separate pharmaceutical compositions, each comprising either a compound of Formula (I), or other compounds disclosed herein, or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

A compound of Formula (I), or other compounds disclosed herein, can be used in therapy in combination with one or more other compounds used to treat a neurodegenerative disease, disorder, or condition. For example, a compound of Formula (I), or other compounds disclosed herein, can be co-administered in combination with one or more other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10, 000:1, and the like. For example, in the treatment of glaucoma, other antiglaucoma medicaments can be used in combination with compounds of Formula (I), or other compounds disclosed herein, including, but not limited to, beta-blockers, including levobunolol (BETAGAN), timolol (BETIMOL, TIMOPTIC), betaxolol (BETOPTIC) and metipranolol (OPTIPRANOLOL); alpha-agonists, such as apraclonidine (IOPIDINE) and brimonidine (ALPHAGAN); carbonic anhydrase inhibitors, such as acetazolamide, methazolamide, dorzolamide (TRUSOPT) and brinzolamide (AZOPT); prostaglandins or prostaglandin analogs such as latanoprost (XALATAN), bimatoprost (LUMIGAN) and travoprost (TRAVATAN); miotic or cholinergic agents, such as pilocarpine (ISOPTO CARPINE, PILOPINE) and carbachol (ISOPTO CARBACHOL); epinephrine compounds, such as dipivefrin (PROPINE); forskolin; or neuroprotective compounds, such as brimonidine and memantine. In certain embodiments, the compound used in combination with a compound of Formula (I), or other compounds disclosed herein, is not an anti-angiogenic agent, such as a steroid derivative, such as 2-methoxyestradiol or analogs or derivatives thereof. In other embodiments, the additional therapeutic agent can be an antibiotic.

The presently disclosed compounds of Formula (I), or other compounds disclosed herein, can be optionally combined with or administered in concert with each other or other agents known to be useful in the treatment of the relevant disease, disorder, or condition. Thus, in the treatment of ALS, for example, the presently disclosed compounds can be administered in combination with Riluzole (RILUTEK), minocycline, insulin-like growth factor 1 (IGF-1), and/or methylcobalamin. In another example, in the treatment of Parkinson's disease, the presently disclosed compounds can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, the presently disclosed compounds can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The presently disclosed subject matter also includes pharmaceutical compositions and kits including combinations as described herein.

In other embodiments, the presently disclosed subject matter includes a combination therapy of administering a compound of Formula (I), or other compounds disclosed herein, in combination with surgery, e.g., surgical relief of intraocular pressure, e.g., via trabeculectomy, laser trabeculoplasty, or drainage implants, and the like.

D. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound of Formula (I), or other compounds disclosed herein, together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly(2-hydroxyethyl-methacrylate) (Langer et al., J. Biomed. Mater. Res. 15:167, 1981; Langer, Chem. Tech. 12:98, 1982), ethylene vinyl acetate (Langer et al., Id) or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, predetermined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of Formula (I), or other compounds disclosed herein, in the manufacture of a medicament for neuroprotection.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to loss of neuronal cells or cell function), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I), or other compounds disclosed herein, employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response, e.g., neuroprotective activity, may be different from the amount of compound effective for another purpose.

In general, a suitable daily dose of a compound of Formula (I), or other compounds disclosed herein, will be that amount of the compound that is the lowest dose effective to produce a therapeutic effect. Such an effective dose will generally depend upon the factors described above. Generally, doses of the compounds of Formula (I) will range from about 0.0001 to about 1000 mg per kilogram of body weight of the subject per day. In certain embodiments, the dosage is between about 1 ng/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

E. Kits or Pharmaceutical Systems

The presently disclosed compounds and compositions can be assembled into kits or pharmaceutical systems for use in treating or preventing neurodegenerative diseases, disorders, or conditions. In some embodiments, the presently disclosed kits or pharmaceutical systems include a compound of Formula (I), or other compounds disclosed herein, or pharmaceutically acceptable salts thereof. In particular embodiments, the compounds of Formula (I), or other compounds disclosed herein, or a pharmaceutically acceptable salt thereof, are in unit dosage form. In further embodiments, the compound of Formula (I), or other compounds disclosed herein, or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a neurodegenerative disease, disorder, or condition. In some embodiments, the instructions include one or more of the following: a description of the active compound; a dosage schedule and administration for treating or preventing a neurodegenerative disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

F. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to the presently disclosed compounds are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —$C(=O)O$— is equivalent to —$OC(=O)$—; —$OC(=O)NR$— is equivalent to —$NRC(=O)O$—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxyl, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2 5}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl(propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$CH_2CH_2CH_2CH_2$—, —$CH_2CH$═$CHCH_2$—, —$CH_2CsCCH_2$—, —$CH_2CH_2CH$($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like). The term "haloaryl," as used herein, however, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

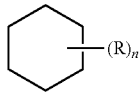

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

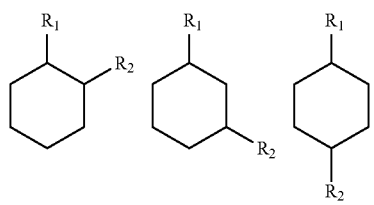

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol

denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

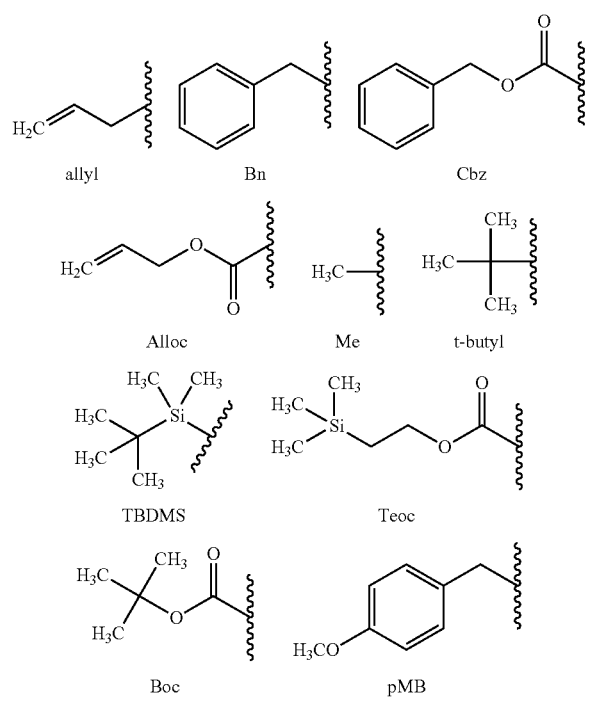

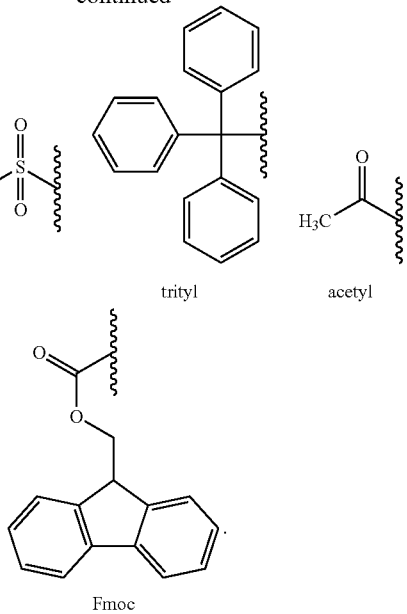

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods

Reagents

Sunitinib, lestaurtinib, crizotinib, axitinib, bosutinib, imatinib, tandutinib, vandetanib, sorafenib and vatalanib were purchased from LC laboratories (Woburn, Mass.), forentinib and KW-2449 were purchased from Selleckchem (Houston, Tex.), and tozasertib from Biovision Life Science (Milpitas, Calif.).

Slow-Release Particles or Formulations

Slow-release particles or formulations, including, but not limited to, polymer, e.g., PLGA, microparticles loaded with sunitinib, SR8165, or tozasertib were prepared using a single emulsion solvent evaporation method. In representative, non-limiting examples, a solution was made by mixing 200 mg of poly(lactic-co-glycolic acid) (PLGA 50:50, 2A, 0.15-0.25 dL/g, MW15K-17K, Lakeshore Biomaterials, Birmingham, Ala.) dissolved in 4 mL methylene chloride with one of various drugs dissolved in DMSO (40 mg sunitinib in 1 mL DMSO, 40 mg SR8165 in 0.5 mL DMSO, 40 mg tozasertib in 1 mL DMSO). The mixture was homogenized at 4000 rpm (Silverson Homogenizer, model L4RT, Chesham Bucks, England) for 1 min into an aqueous solution containing 1% polyvinyl alcohol (PVA, MW=25 KDa, Polysciences, Warrington, Pa.). The particles were then stirred for 2 hours to allow hardening, collected by centrifugation at 5000 g for 5 minutes, washed with deionized water 3 times, and freeze-dried to a powder that could be reconstituted prior to administration. Microparticle size was determined using a Coulter Multisizer IIe (Beckman-Coulter Inc., Fullerton, Calif.). To determine the drug release rate in vitro, 5 mg of drug-loaded particles were suspended in 2 mL of phosphate-buffered saline (pH 7.4) and incubated at 37° C. on a rotator (Tang et al., 2010). At selected time points, microparticles were precipitated by centrifugation, and the supernatant removed and replaced with 2 mL of fresh phosphate buffer. Supernatants were analyzed by spectrophotometry at 420 nm for sunitinib and SR8165, and 252 nm for tozasertib.

Statistical Analysis

All statistical analyses were performed with the unpaired Mann-Whitney-Wilcoxon test.

RGC Purification, Culture, Screening and Imaging

All animal use was in accordance with ARVO Statement for the Use of Animals, and all the experimental procedures were performed in compliance with animal protocols approved by the IACUC at Johns Hopkins University. Retinas were isolated from postnatal 0-5 day mice and dissociated with papain. Microglia was immunodepleted with anti-CD11b conjugated Dynabeads. The suspension of retinal cells were immunopanned on plates pre-conjugated with anti-Thy1.2 antibody (Serotec, Raleigh, N.C.; MCA028) and goat anti-mouse IgM (Jackson Immunoresearch) at room temperature (RT). After washing, RGCs were released from the plate by a cell lifter, counted, and seeded at a density of 10,000 per well in 96-well plates in the media composed of Neurobasal, B27, N2 supplement, L-glutamine, and penicillin/streptomycin. After a 72 hour culture at 37° C., RGCs were stained with calcein AM, ethidium homodimer, and Hoechst 33342. Images were taken from portions of each well with Cellomics Kinetscan or Cellomics ArrayScan VTI HCS Readers (Thermo Fisher), and cell survival was quantified and calculated with the algorithms in Cellomics Neuroprofiling package. As indicated, RGC viability was alternatively measured by CellTiter-Glo luminescence (Promega, Fitchburg, Wis.).

For siRNA-based screening, the siRNAs from the Sigma Mission Mouse Kinome library were complexed with NeuroMag (Oz Biosciences, Marseille, France) at a final concentration of 20 nM. RGCs were then reverse transfected on a stationary magnet and assayed for survival 72 hours later using CellTiter-Glo (Promega). Oligonucleotides conferring survival more than 3 SD from the nontargeting siRNAs were considered neuroprotective (106 siRNA, 5.4%). Confirmatory siRNAs were obtained from both Dharmacon (Lafayette, Colo.) and Ambion (Carlsbad, Calif.). Adenovirus expressing wildtype or kinase-dead DLK (Robitaille et al., 2004) was added to RGCs at a multiplicity of infection of 100-1000. For small molecule-based screening, serially diluted compounds in DMSO were transferred to 1536 well assay plates by a 23 nL pintool array (Kalypsys, San Diego, Calif.), with a final concentration of 0.057% DMSO for each respective compound concentration. RGCs were cultured for 48 h, and cell viability was analyzed on a plate reader (ViewLux, Perkin Elmer, Waltham, Mass.) using the bioluminescent CellTiterGlo (Promega, Fitchburg, Wis.) assay. Concentration response curves were created using CurveFit (NIH NCATS). The screened libraries include the modified Tocriscreen (1395 compounds) collection, FDA-approved drugs (2814 compounds), LOPAC (1208 compounds) and PTL2/PTL3 (based on pteridin, pyrimidine and quinazoline scaffolds; 2319 compounds).

Rat Intravitreal Injections 6-week old male Wistar rats were anesthetized with ketamine/xylazine. A partial periotomy was made to expose the sclera. The injection site was approximately 1 mm posterior to the ora serrata, and the injection glass pipet was angled towards the optic disc in order to avoid lens injury. 5 µL (10 µg) of PLGA microspheres were injected with a glass pipet and Hamilton syringe.

Rat Optic Nerve Transection

The optic nerve was exposed by a partial peritomy and intraorbital dissection of the extraocular muscles, and then transected with a 25-gauge needle. 4-Di-10-ASP were then applied to the proximal nerve stump. Care was taken to avoid vascular injury during the transection, and retinal perfusion was examined after nerve transection. Two weeks after transection, rats were sacrificed and enucleated. Retinas were flatmounted, imaged with confocal microscopy and the number of 4-Di-10-ASP-labeled cells with RGC morphology was quantified. Imaging and quantification of RGC survival were performed in a masked fashion.

Rat Laser-Induced Ocular Hypertension

Intraocular pressure (TOP) was unilaterally elevated by laser treatment of the trabecular meshwork as previously described (Levkovitch-Verbin, H. et al., 2002). Briefly, 6-week old Wistar male rats were anesthetized with ketamine/xylazine. On two consecutive weeks, 40-50 532 nm diode laser spots were applied to the prelimbal region (50 µm diameter, 600 mW power and 0.6 seconds duration). Under anesthesia, the IOP of laser-treated and fellow eyes was measured with TonoLab one and three days after laser treatment. Four weeks following laser treatment, rats were perfused with 4% paraformaldehyde in phosphate buffer. Optic nerves were isolated, postfixed with 1% osmium tetroxide, embedded in epoxy resin and stained with 1% toluidine blue. Images from 10 random and nonoverlapping fields were taken with 100× oil phase contrast objective. The area of entire optic nerve cross-sections were imaged with 10× magnification, and used with axon counts from the 10 field to derive axon counts per nerve. The laser treatment and acquisition of optic nerve images were performed in a masked fashion.

Mouse Intravitreal Injection and Optic Nerve Crush

Three-month old male C57BL/6 and Dlk floxed mice (BL/6 background) were anesthetized with ketamine/xylazine and intravitreally injected with $10^{10}$ DNA-containing particles of capsid-mutant (Y444, 500, 730F) AAV2 expressing Cre recombinase from the chicken β-actin promoter. Seven days later, optic nerve was surgically exposed and crushed with Dumont N5 self-closing forceps 1 mm behind the globe for 3 seconds. 10 days following nerve crush, eyes were enucleated, fixed and RGC survival was measured with flatmount immunostaining for βIII-tubulin and Brn3. Intravitreal injection, optic nerve crush, immunofluorescence and RGC counting were performed in a masked fashion.

Western Blots, Immunofluorescence and RT-PCR

Western blots were performed according to the standard protocol. The following antibodies were from Cell Signaling Technology (Beverly, Mass.): Phospho-JNK, Thr183/Tyr185 (4671); JNK (9258); Phospho-MKK7 (4171), and MKK7 (4172). Monoclonal anti-alpha-tubulin antibody (T6074) was purchased from Sigma (St. Louis, Mo.), βIII tubulin (TUJ1) from Covance, goat polyclonal Brn3 from C-13, and rabbit anti-Cre from Novus. DLK rabbit polyclonal was provided by S. Hirai.

Retinal immunofluorescence was performed following standard protocols. The following antibodies were used: mouse neuronal class βIII tubulin (clone TUJ1, 1:500, Covance, Princeton, N.J.), rabbit polyclonal anti-DLK (1:200, S. Hirai), and goat polyclonal Brn3 (C-13, 1:100), rabbit anti-Cre (1:100, Novus Biologicals, Littleton, Colo.).

Dlk mRNA levels were measured with RT-PCR with the following primer set: 5'-ATTCCTCAGCCATCATCTGG-3' and 5'-ATTTCGTGGTTTGCTGTTCC-3'.

Electrophysiology

Recordings were made by using the whole-cell patch-clamp technique in both current- and voltage-clamp modes with an Axopatch 200B. Data were low-pass filtered at 1 kHz (Bessel) and sampled at 10 kHz. A liquid junction potential of −2 mV has been corrected, and the resting potential was estimated to be −62±2.2 mV (Mean±SEM, n=13). The recording pipette was filled with the following intracellular solution (in mM): 100 K-gluconate, 50 KCl, 20 HEPES, 10 EGTA, 5 $MgCl_2$, 2 ATP, 0.1 GTP, pH adjusted to 7.33 with KOH. The cells were continuously perfused with (in mM): 140 NaCl, 5 KCl, 1 $MgCl_2$, 2.5 $CaCl_2$, 10 glucose, 10 HEPES, pH 7.4 with NaOH.

Production of AAV Vectors.

AAV vector preparations were produced by the 2-plasmid, co-transfection method with modifications (Zolotukhin, S. et al., 2002). Briefly, approximately $10^9$ HEK 293 cells were cultured in DMEM with 5% fetal bovine serum and antibiotics. DNA transfection of the two vector plasmids by CaPO4 precipitation then were allowed to incubate at 37° C. in 7% $CO_2$ for 60 h. The cells were then harvested, lysed by three freeze/thaw cycles, the crude lysate clarified by centrifugation and the resulting vector-containing supernatant run on a discontinuous iodixanol step gradient. The vector-containing fraction were further purified and concentrated by column chromatography on a 5-ml HiTrap Q Sepharose column using a Pharmacia AKTA FPLC system. The vector is eluted from the column using 215 mM NaCl, pH 8.0, and the AAV peak collected, concentrated and buffer exchanged into Alcon BSS with 0.014% Tween 20. Before release, vector purity was assessed by silver-stained SDS-PAGE, a negative bioburden test, and an endotoxin test in the acceptable range. Finally, vector was titered for DNase-resistant vector genomes by Real-Time PCR relative to a reference AAV vector standard.

Example 2

High Content Screening Assay of Small Molecule Libraries

Glaucoma is the leading cause of irreversible blindness worldwide (Quigley and Broman, 2006). It is a neurodegenerative disease in which vision loss is caused by the axonal injury and death of RGCs (Howell et al., 2007), the projection neurons that process and transmit vision from the retina to the brain. Current therapies (i.e. surgery, laser and eye drops) all act by lowering intraocular pressure (IOP). Pressure reduction, however, can be difficult to achieve, and even with significant pressure lowering, RGC loss can continue. Efforts have therefore been made to develop neuroprotective agents that would complement IOP lowering therapies by directly inhibiting the RGC cell death process (Danesh-Meyer and Levin, 2009; Chang and Goldberg, 2012; Limb and Martin, 2011). No neuroprotective agent, however, has been approved for clinical use.

Protein kinases provide attractive targets for the development of neuroprotective agents. A number of kinases, including cyclin-dependent kinases, death-associated protein kinases, c-Jun N-terminal kinases (JNK1-3), mitogen-activated protein kinases (MAPKs), and glycogen synthase kinase-3β, are involved in neuronal cell death (Tu et al., 2010; Subramaniam and Unsicker, 2010; Wang et al.; Hisanaga and Endo, 2010; Sun et al., 2011; Ribas et al., 2011; Bessero et al., 2010; Fernandes et al., 2012). An additional attraction is that protein kinases are readily druggable. The pharmacology and medicinal chemistry of kinase inhibitors are well-developed, with kinases now being the most important class of drug targets after G-protein-coupled receptors (Cohen, 2002). Although the primary clinical use of kinase inhibitors continues to be as anti-neoplastic agents, increasing attention is being paid to their use in other areas (Scott, 2011; Satoh et al., 2011). In order to identify, in a comprehensive and unbiased manner, kinases that could serve as novel targets for neuroprotective glaucoma therapy, the entire mouse kinome was screened for kinases whose inhibition promotes RGC survival. For this screen, a high-throughout method was developed for transfecting primary RGCs with small interfering RNA ligonucleotides (siRNAs) and coupled with a quantitative assay of RGC survival.

Figure 2:
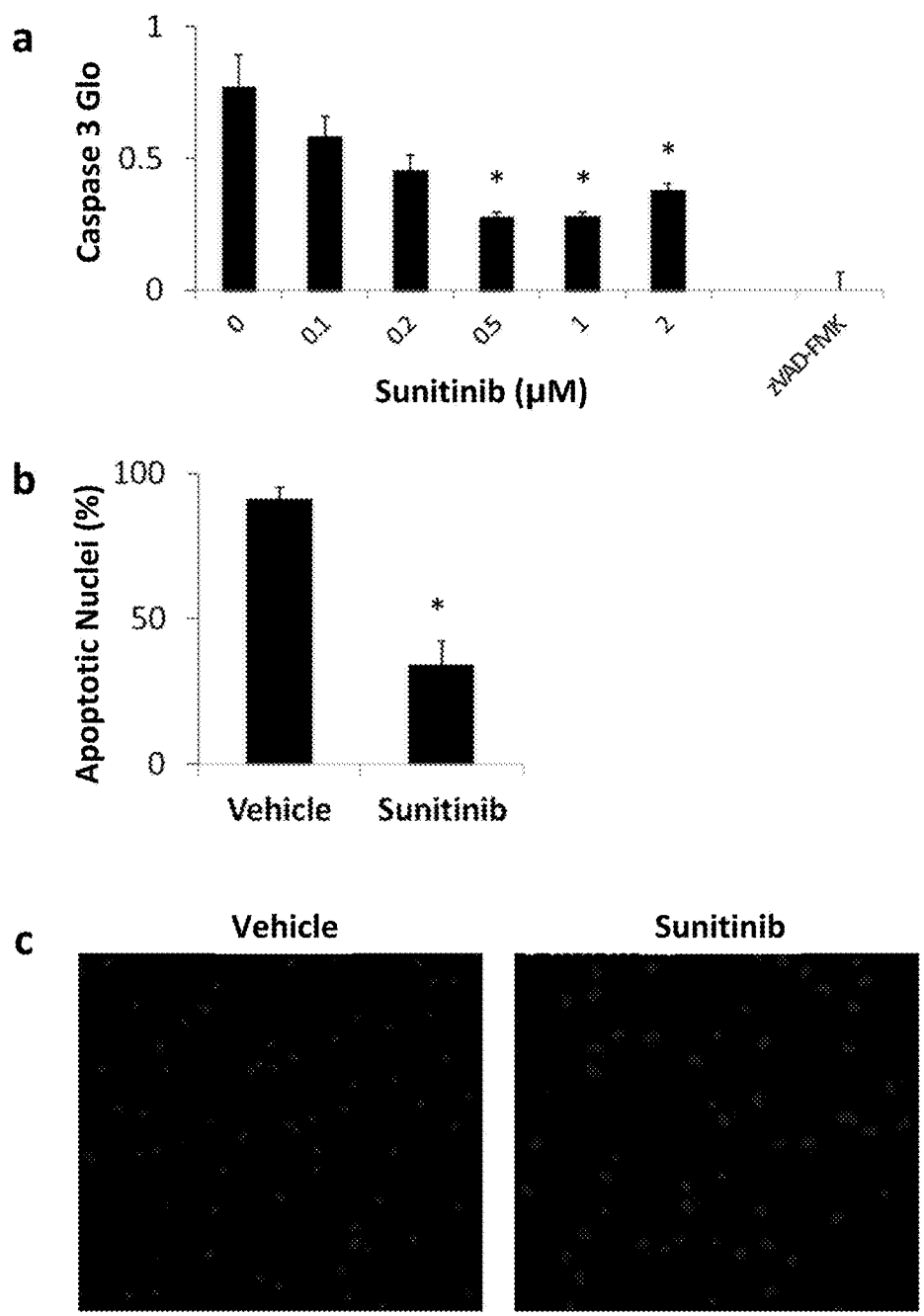

In order to identify novel neuroprotective agents, a high-content, high-throughput, phenotypic screen was developed using primary RGCs. RGCs were immunopanned from perinatal mice using an antibody against the RGC surface antigen Thy1 (Barres et al., 1988), arrayed into microtiter (96- to 1536-well) plates, and cell survival in the presence of various bioactive small molecules was assayed 72 hours later. Screening over 6,000 unique compounds at multiple doses (Inglese, 2006) repeatedly identified sunitinib and related oxindole analogs as being highly neuroprotective. Sunitinib treatment led to a dose-dependent increase in the viability of primary RGCs, with maximal activity between 0.5 and 1 µM (FIG. 1A). Increased survival was associated with a corresponding decrease in markers of apoptosis, including caspase activation, nuclear condensation and fragmentation (FIG. 2).

Example 3

RGC Cell Survival Assay with Murine Purified RGCs

Next, the ability of sunitinib to rescue RGC death in vivo in response to optic nerve transaction was tested. Sunitinib, or its vehicle control, were packaged in poly(lactic-co-glycolic acid) (PLGA)-based, slow-eluting microspheres (Edwards, 1997) and injected intravitreally into Wistar rats. Seven days later, optic nerves were transected and RGCs were retrogradely-labeled by applying 4-Di-10-ASP to the proximal nerve stump. At two weeks post-transection, sunitinib-treated compared to control animals showed a 3-4 fold increase in surviving RGCs (FIG. 1B). To evaluate sunitinib's neuroprotective activity in a glaucoma model, rats were pretreated with intravitreal vehicle- or sunitinib-eluting microspheres and then diode laser treatment of the trabecular meshwork was used to increase IOP (FIG. 3) (Levkovitch-Verbin, H. et al., 2002). In eyes injected with control microspheres, there was a 58% reduction in optic nerve axons at one month. In eyes treated with sunitinib-eluting microspheres, however, axon loss was reduced by 40% (p<0.05, FIG. 1C). SR8165, a sunitinib-analog found to have greater efficacy in vitro (FIG. 5), conferred similar neuroprotection upon delivery from PLGA microspheres (FIG. 1C). Together, these results establish sunitinib, and related oxindole analogs, as potential neuroprotective agents for glaucoma.

To evaluate tozasertib's neuroprotective activity in a glaucoma model, rats were pretreated with intravitreal tozasertib- or vehicle-eluting microspheres and then diode laser treatment of the trabecular meshwork was used to increase IOP (FIG. 4A) (Levkovitch-Verbin H et al., 2002). A pretreatment paradigm is appropriate given that glaucoma in humans is thought to result from chronic, repeated injury and thus drug administered at any point in the disease is likely to impact future degeneration. The drug- and vehicle-treated eyes showed similar degrees of IOP elevation (FIG. 20B). In eyes injected with control microspheres, there was a 60% reduction in optic nerve axons at one month. In eyes treated with tozasertib-eluting microspheres, however, axon loss was decreased by 39% (FIGS. 20B and 4C).

Figure 5:
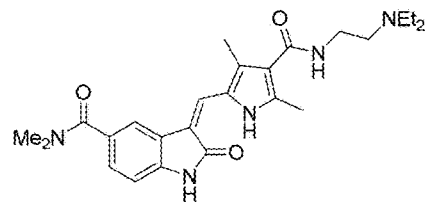
Figure 5:
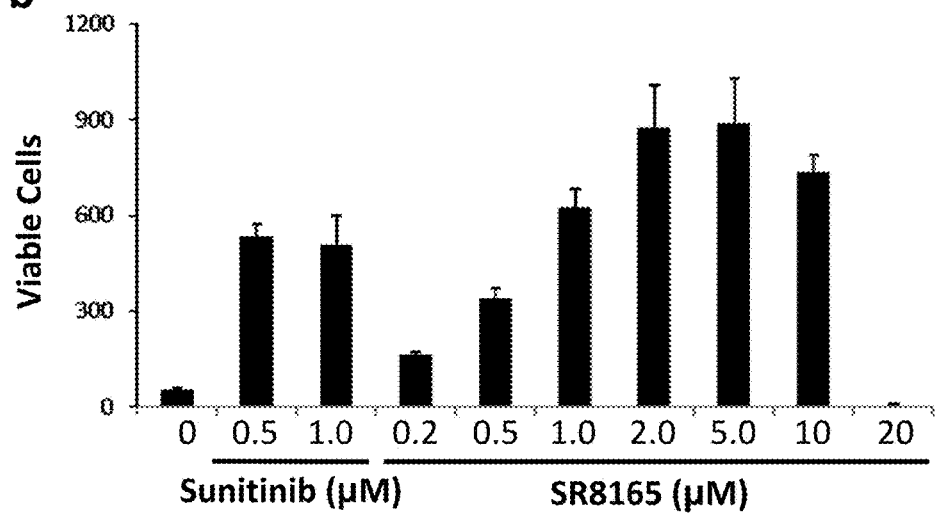
Figure 5:
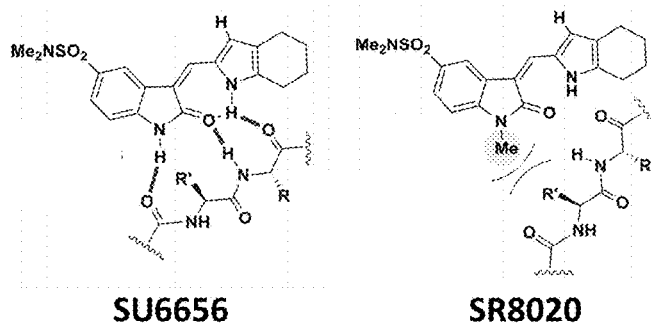
Figure 6:
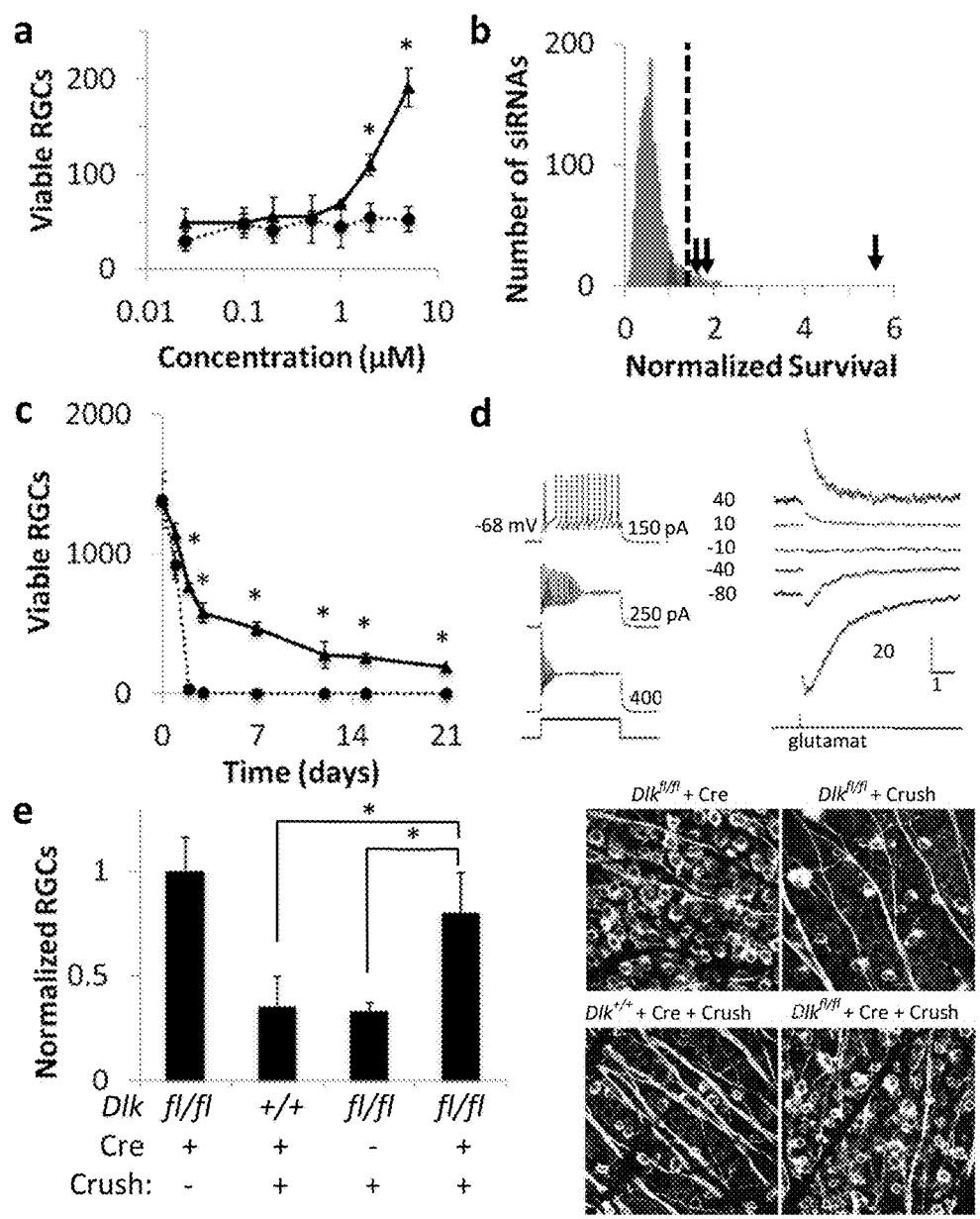

To confirm that kinase inhibition mediated the neuroprotective activity of these oxindole kinase inhibitors, the activity of SU6656, a neuroprotective analog of sunitinib, was compared to that of SR8020, an otherwise identical derivative in which a hydrogen to methyl group substitution is predicted to disrupt the binding to the kinase ATP-binding pocket (Lackey, 2000; FIG. 5). SR8020 failed to show survival-promoting activity, thus suggesting that the neuroprotective activity of sunitinib and its analogs is mediated through ATP-competitive kinase inhibition (FIG. 6A). At neuroprotective concentrations, sunitinib inhibits nearly 200 kinases (Davis, 2011).

Among the kinases potently inhibited are vascular endothelial growth factor receptor 2 (VEGFR2), c-Kit, FLT3 and platelet-derived growth factor receptors (PDGFRs; OFarrell, 2003). Other small molecules, however, known to inhibit one or more of those same receptor tyrosine kinases, including imatinib, sorafenib, tandutinib, vandetanib, and vatalanib, all lack neuroprotective activity (FIG. 9). These results, together with the relatively high concentrations required for neuroprotection in vitro, suggested that the kinase(s) whose inhibition promotes RGC survival are one or more low-affinity targets of sunitinib. To identify the relevant kinase(s), the primary RGC platform for an unbiased RNA interference-based screen of the entire mouse kinome was adapted. Without wishing to be bound to any one particular theory, it was reasoned that kinases, whose knockdown increased RGC survival, would represent possible relevant targets for neuroprotective kinase inhibition.

Figure 7:
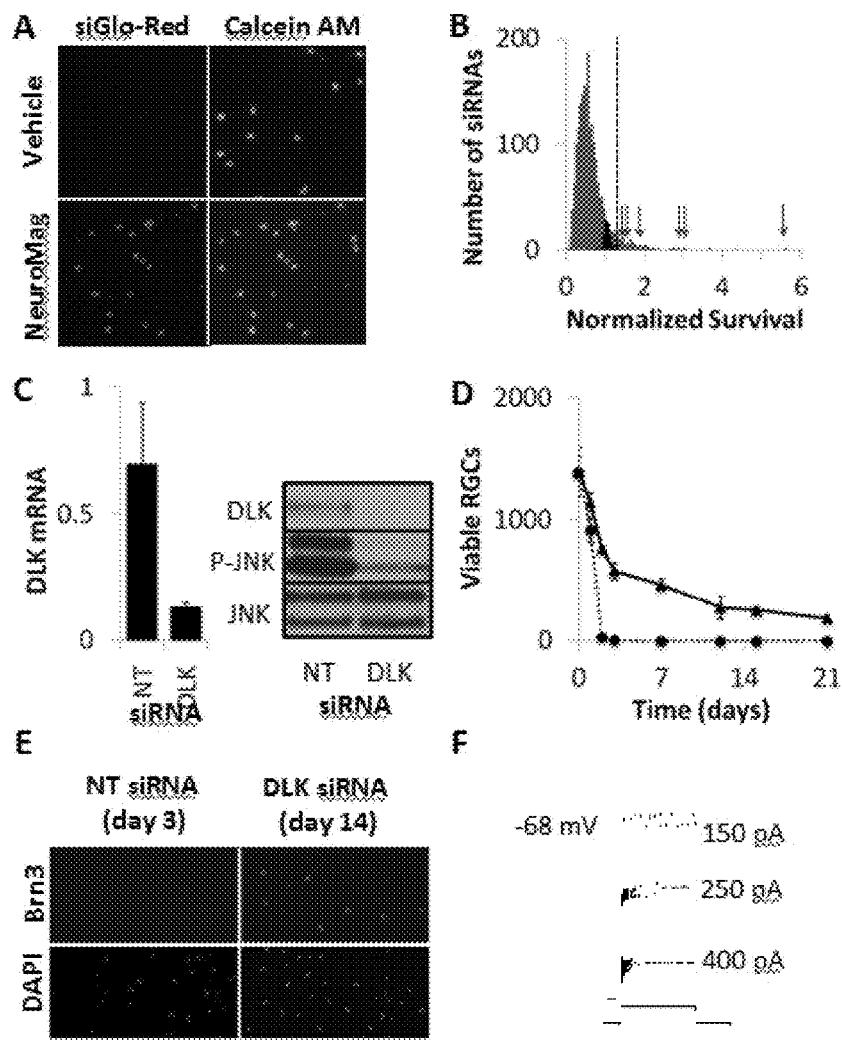
Figure 10:
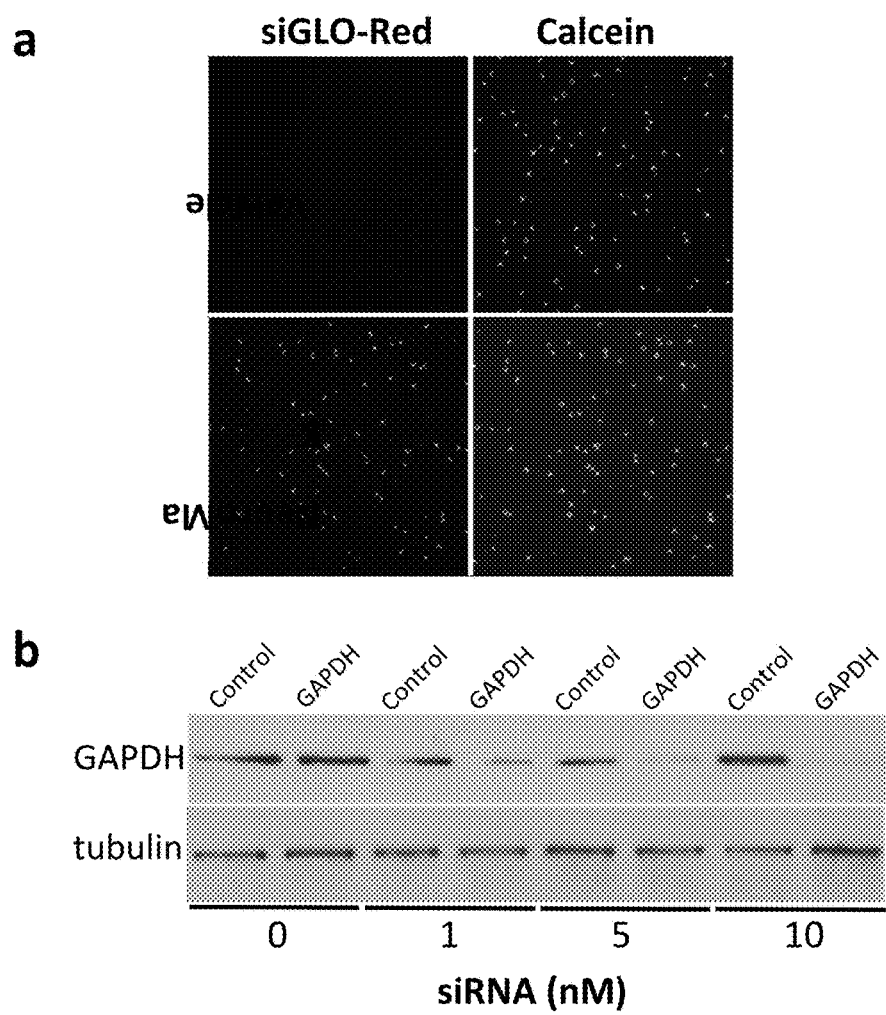

To develop a biologically relevant RGC survival assay, primary RGCs were used, immunopanned from perinatal mice (Barres et al., 1988). Despite the inherent challenges in the use of primary neurons, they were more likely than established cell lines to be predictive of in vivo efficacy (Sharma et al., 2012). Individually inhibiting the function of each kinase in the genome required an efficient method for siRNA delivery to the primary RGCs. Since traditional transfection procedures were either toxic or minimally effective with RGCs, a magnetic nanoparticle-based reagent (NeuroMag) was adapted for high-efficiency, high-throughput siRNA delivery (FIGS. 7A and 10). NeuroMag based transfection resulted in consistent and efficient suppression of target gene expression in unselected RGC populations (FIG. 15). Using this approach, an arrayed library of 1869 siRNAs wa screened against 623 kinases, providing three-fold coverage of the mouse kinome, for the ability to promote the survival of RGCs grown in neurotrophin-deficient media (FIGS. 6B and 7B). In order to minimize the number of false-positive leads resulting from off-target silencing, the conservative approach was taken of focusing only on kinases for which all three siRNAs were protective. Indeed, only two kinases met this criterion, mitogen-activated protein kinase kinase kinase 12/dual-leucine zipper kinase (Map3k12/Dlk) and its only known substrate, mitogen-activated protein kinase kinase 7 (Map2k7/Mkk7) (Merritt et al., 1999). Secondary testing, using an independent set of siRNA with distinct targeting sequences, confirmed that both kinases were the relevant targets (FIG. 11). Supporting the biological relevance of this finding, MKK7 and its homolog, MKK4, are the canonical activators of JNK1-3 (Tournier et al., 1997), key regulators of RGC cell death (Sun et al., 2011; Ribas et al., 2011, Bessero et al., 2010; Fernandes et al, 2012).

The kinetics of RGC cell death following DLK knockdown was studied next. Immunopanned RGCs were transfected with Dlk siRNA, or a nontargeting control, and followed over time. By 24 hours, Dlk siRNA efficiently reduced DLK expression at both the mRNA and protein levels. Consistent with DLK being a major activator of JNK in injured RGCs, DLK knockdown inhibited JNK phosphorylation, indicating attenuation of downstream JNK signaling (FIG. 7C). By 48 hours there was a clear survival effect (FIG. 7D). While there were very few live control cells, RGCs transfected with Dlk siRNA had greater than 50% viability. The prosurvival effect of DLK inhibition persisted for at least 3 weeks. It was found that Dlk mRNA levels stayed low throughout this period (data not shown), consistent with reports that siRNA knockdown in post-mitotic neurons can be long-lived (Tanaka et al, 2011; Tanaka et al., 2009). Axonal injury typically reduces the expression of many RGC-specific markers secondary to the downregulation of the Brn3 family of transcription factors (Yang et al., 2007). In RGCs with DLK knockdown, however, Brn3 continued to be expressed (FIG. 7E). This results suggested that DLK may be a relatively upstream injury signal and that injured RGCs, in the absence of DLK signaling, maintain characteristics of uninjured RGCs. At the functional level, patch-clamp recordings showed that RGCs kept alive for two weeks with Dlk siRNA continue to generate action potentials in response to depolarizing current (FIG. 7F). Without wishing to be bound to any one particular theory, the results shown herein thus suggest that DLK may be the as-yet-unidentified trigger for JNK activation and cell death in RGCs. Indeed, DLK has been shown to mediate developmental apoptosis in peripheral motor and sensory neurons, but no role in adult CNS neurodegenerations has been firmly established (Itoh et al., 2011; Ghosh et al., 2011).

Figure 12:
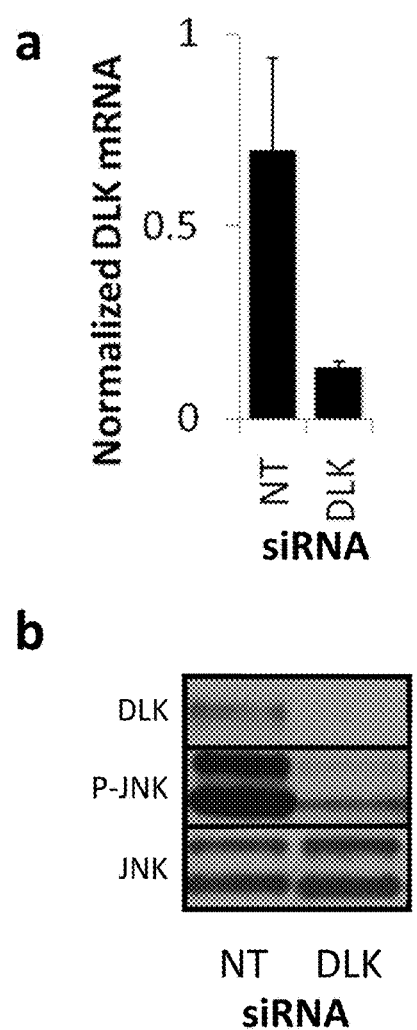

To explore the role of DLK in mediating RGC death, immunopanned RGCs were transfected with DLK siRNA, or a nontargeting control, and survival was followed over time. As predicted, DLK siRNA knocked down the level of DLK mRNA and protein and inhibited phosphorylation of JNK, a marker of activation of JNK downstream signaling (FIG. 12). While nontargeting siRNA-transfected cells were dead by 72 hours, RGCs transfected with DLK siRNA survived for greater than 3 weeks (FIG. 6C). To determine whether the RGCs that are kept alive for extended periods with DLK siRNA or sunitinib treatment remain functional, patch-clamp recordings were performed at two weeks in culture. Consistent with persistent functionality, the RGCs conducted action potentials in response to depolarizing current and were responsive to exogenously applied glutamate (FIG. 6D). To test the role of DLK in vivo in response to axonal injury, mice carrying a floxed allele of Dlk (Miller et al., 2009) were intravitreally injected with capsid-modified adeno-associated virus 2 (AAV2) (Petrs-Silva, 2009; Petrs-Silva, 2011) expressing the P1 bacteriophage recombinase Cre. After sufficient time for Cre-mediated deletion of Dlk (FIG. 12), eyes were subjected to optic nerve crush. Compared to either Dlk$^{+/+}$ mice injected with AAV2-Cre or Dlk$^{fl/fl}$ mice in the absence of Cre, Dlk$^{fl/fl}$ mice injected with AAV2-Cre had a 75% reduction in RGC loss (FIGS. 6E and 8).

As DLK appears to be a critical mediator of RGC cell death in vitro and in vivo, the mechanism of DLK regulation was examined next. Surprisingly, and unlike other members of the JNK cascade, DLK protein is undetectable in uninjured RGCs both in vitro and in vivo (FIGS. 14a and 14b-left panel). After immunopanning in vitro (when RGCs are necessarily axotomized and injured), optic nerve crush (data not shown), or transection in vivo, however, a robust upregulation of DLK protein was observed (FIGS. 14A and 14B-right panel). In contrast, Dlk transcript levels remained relatively constant after injury (FIG. 14A), indicating increased translation and/or decreased protein turnover as the mechanism mediating DLK upregulation. In *D. melanogaster*, the DLK homolog, Wallenda, is post-translationally regulated by the E3 ubiquitin ligase Highwire (Collins et al., 2006). Mice with a brain-specific conditional knockout of Phr1 (the vertebrate Highwire homolog), however, show no difference in the overall brain levels of DLK protein (Bloom et al., 2007). Furthermore, knockdown of PHR1 in the cultured RGCs did not affect DLK levels (data not shown). Without wishing to be bound to any one particular theory, this data suggests that either PHR1 regulates DLK levels only in certain settings/neuronal subtypes or that DLK levels in vertebrates are regulated by another unidentified gene.

To directly test the hypothesis that increased DLK protein can trigger RGC cell death, adenovirus was used to overexpress GFP, DLK or a kinase-dead (KD) version of DLK (K185R) (Robitaille et al., 2004). Primary RGCs were infected and survival measured 48 hours later. Consistent with the suggested model, wildtype DLK overexpression hastened cell death, while overexpression of K185R DLK functioned as a dominant-negative, as assessed by JNK phosphorylation, and actually increased survival (FIG. 14C).

Figure 16A:
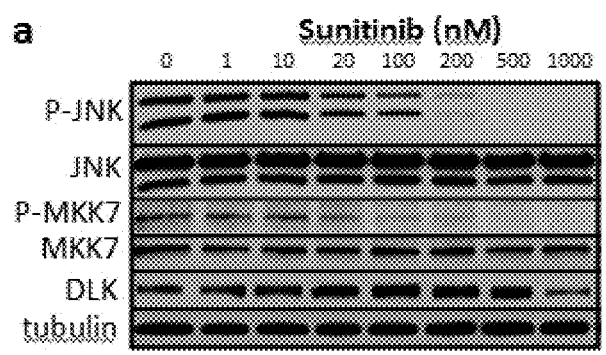
Figure 16B:
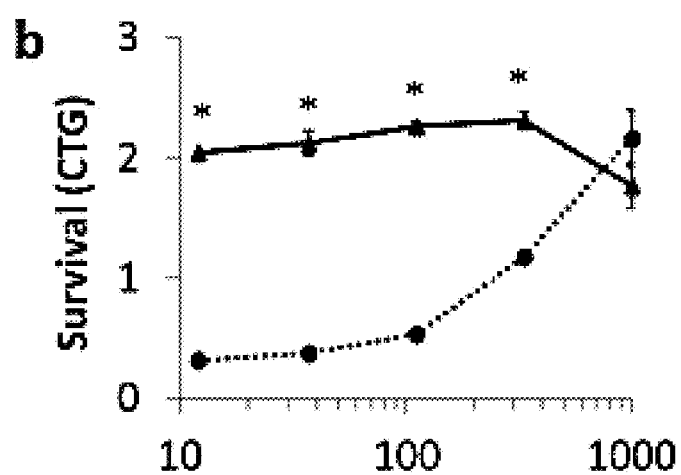
Figure 16C:
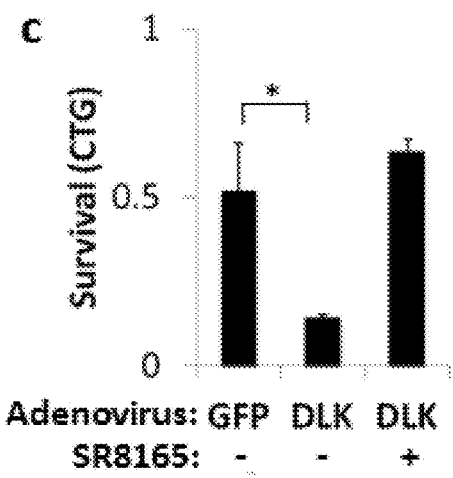

Given that both sunitinib treatment and DLK knockdown promote RGC survival, the simplest explanation was that sunitinib's neuroprotective activity was mediated, at least in part, by DLK pathway inhibition. Indeed, although published kinase inhibitor profiling indicates that sunitinib does not have significant affinity for JNK1/2/3 or MKK4/7, it does bind DLK at the neuroprotective concentrations shown herein (Davis et al., 2011; Karaman et al. 2008). To assess sunitinib's effect on DLK signaling in RGCs, immunopanned cells were cultured in the presence of increasing amounts of sunitinib. The same concentrations that increase RGC survival caused a decrease in the phosphorylation of targets downstream of DLK, including MKK7 and JNK (FIG. 16A). This suggested that modulation of DLK signaling was part of the mechanism of sunitinib's neuroprotective activity. It was postulated that if DLK were a key biologically-relevant target of sunitinib, then RGCs transfected with DLK siRNA (and thus with only residual DLK activity) should demonstrate little additional survival benefit from addition of sunitinib. Indeed, while sunitinib significantly increased the survival of control-transfected cells, it had little, if any, effect on DLK siRNA-transfected RGCs (FIG. 16B). Yet another prediction of the suggested model is that sunitinib should mitigate the toxicity from adenoviral-overexpressed DLK. To test this prediction, however, the concentrations of sunitinib had to be increased and were limited by its cytotoxicity at high concentrations. Instead, SR8165 was used, a sunitinib analog with a widened therapeutic window, and it was found that DLK toxicity was in fact reduced by SR8165 treatment (FIG. 16C).

Figure 16D:
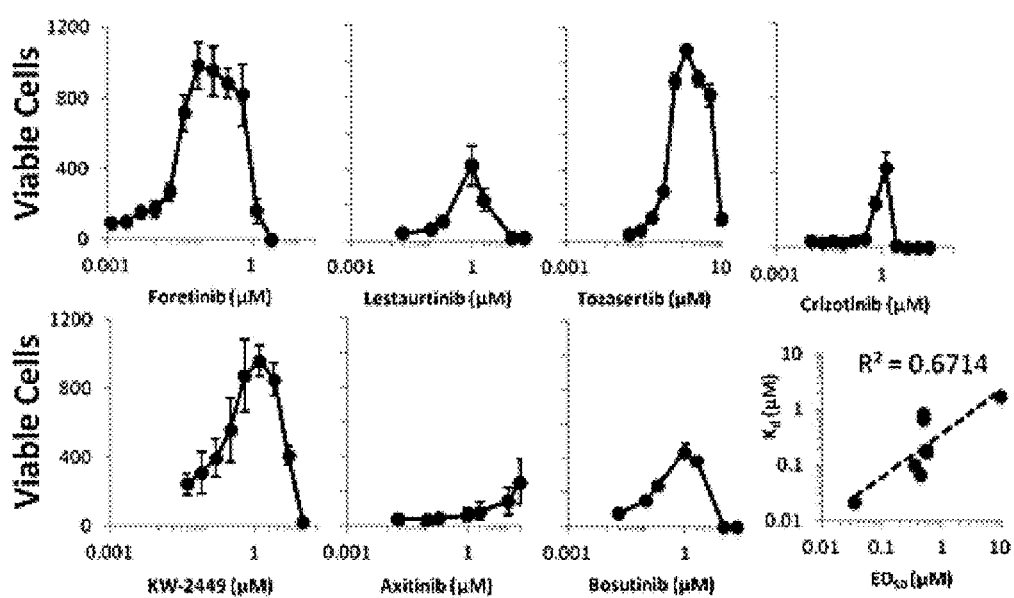

It was reasoned that if sunitinib's neuroprotective activity was mediated, at least in part, by direct DLK inhibition, then other small molecule DLK inhibitors should also be neuroprotective. Using published kinase inhibitor profiles, nine compounds reported to bind DLK (axitinib, bosutinib, neratinib, crizotinib, tozasertib, lestautinib, foretinib, TAE-684 and KW-2449) (Davis et al., 2011) were tested. Except for neratinib and TAE-684, which were limited by toxicity at nanomolar doses, the remaining kinase inhibitors all promoted the survival of primary RGCs in culture, with neuroprotective doses that roughly correlated with their biochemical affinity for purified DLK (FIG. 16D). To confirm these findings in vivo, intravitreal tozasertib was tested in a slow release formulation, and found that it protected RGCs in both the optic nerve transection and glaucoma models (FIG. 19).

A similar experiment was performed demonstrating the neuroprotective activity of foretinib, cabozantinib, crizotinib, KW-2449, bosutinib, axitinib, and dasatinib with sunitinib as a positive control (FIGS. 17 and 18).

The siRNA and conditional knockout results implicated DLK as a key mediator of RGC cell death. Thus, as a prototype for drug-development, it was explored whether pharmcologic inhibition of DLK would be neuroprotective. Several small molecule kinase inhibitors were tested that had previously been shown to bind DLK at submicromolar doses (Karaman et al., 2008; Davis et al., 2011) for their ability to promote RGC survival in culture (FIG. 16). Tozasertib, a small molecule originally developed as an aurora kinase inhibitor for cancer treatment (Harrington et al., 2004), showed significant neuroprotective activity, demonstrating increased RGC survival in a dose-dependent manner (FIG. 19A). Furthermore, the same concentrations that increased RGC survival caused a decrease in the phosphorylation of targets downstream of DLK, including MKK7 and JNK (FIG. 19B). This effect is unlikely due to direct inhibition of MKK7 and/or JNK as published kinase inhibitor profiling data indicates that tozasertib does not have significant affinity for either kinase (Karaman et al., 2008; Davis et al., 2011). Given tozasertib's ability to inhibit multiple kinases, it was desired to more directly test whether its neuroprotective activity involved DLK inhibition. It was postulated that if DLK were a key biologically-relevant target of tozasertib, then reducing the amount of DLK with siRNA should sensitize the cells to lower doses of tozasertib (FIG. 19C). Indeed, RGCs transfected with DLK siRNA had a left-shift of the tozasertib-survival dose-response curve compared to RGCs transfected with a control siRNA. Without being bound to any one particular theory, yet another prediction of the model is that increased levels of DLK should necessitate higher levels of tozasertib to achieve the same amount of survival. As expected, RGCs transduced with adenovirus overexpressing DLK had a right-shift of the tozasertib-survival dose-response curve compared to control adenovirus-transduced cells (FIG. 19D).

Next, the ability of tozasertib to promote RGC survival was tested in vivo. The ability of tozasertib to promote RGC survival was tested following optic nerve transection. To provide sustained, local ocular drug delivery, tozasertib-containing, poly(lactic-co-glycolic acid) (PLGA)-based, slow-eluting microspheres were generated (Edwards et al., 1997). For these experiments, rats were chosen over mice because their larger eye size is more amenable to microsphere injection. Wistar rats were pretreated with intravitreal microspheres containing tozasertib or vehicle. Seven days later, optic nerves were transected and RGCs were retrogradely-labeled by applying the lipophilic tracer, 4-Di-10-ASP, to the proximal nerve stump (Pavlidis and Fischer, 2000). Two weeks after transection, retinal flatmounts were examined by confocal microscopy to identify and quantify the number of surviving RGCs. Vehicle-treated eyes showed an average of 12.0% surviving RGCs compared to 32.3% surviving cells in the tozasertib-treated eyes (FIG. 20A).

A novel high-content phenotypic screen based on primary RGC cultures described herein unexpectedly identified sunitinib, a broad-spectrum receptor tyrosine kinase inhibitor that induces apoptosis in cancer cells (OFarrell et al., 2003), as a novel neuroprotective agent capable of promoting RGC survival in vitro and in vivo, including in a rodent model of glaucoma. In rodent glaucoma and traumatic optic neuropathy models, sunitinib protects RGCs from cell death. In order to identify the molecular target(s) through which sunitinib promotes RGC survival, a high-throughput RNA interference-based assay was developed, and used to screen the full mouse kinome. The screen identified dual-leucine zipper kinase (DLK) as a key neuroprotective drug target of sunitinib. Supporting this finding, a number of other neuroprotective kinase inhibitors also inhibit DLK. Furthermore, it was shown that DLK undergoes a robust post-transcriptional upregulation in response to injury that is both necessary and sufficient for RGC cell death. Together, these results establish a novel drug/drug target combination in glaucoma and suggest a possible biomarker for RGC injury.

Although initially a paradoxical finding, given sunitinib's inhibition of growth receptor signaling and stimulation of apoptosis, without wishing to be bound to any one particular theory, it is believed that sunitinib's neuroprotective activity is likely mediated through inhibition of JNK signaling, via the DLK pathway, providing a mechanistic explanation for its neuroprotective activity. These results establish a novel therapeutic strategy for the treatment of glaucoma and related optic neuropathies, and may also have relevance to other CNS neurodegenerations.

Large-scale RNAi-based phenotypic screens in lower organisms have successfully identified genes involved in the rescue of neuronal degenerations (Bhattacharya et al., 2012; Dimitriadi et al., 2010; Schulte et al., 2011). Parallel screens utilizing primary vertebrate neurons, however, have been more difficult due to the challenges working with and transfecting primary neuronal cell cultures. Using a magnetic nanoparticle-based method, easily compatible with automation, the presently disclosed subject matter has overcome these challenges and shows the results of performing the first kinome-wide survival screen using a disease-relevant primary neuron. This global and unbiased approach led to the identification of DLK signaling as a key cell death pathway in RGC degeneration. Moreover, it establishes the proof-of-principle for a whole-genome scan in primary RGCs to identify additional potential neuroprotective pathways and drug targets.

Several previous studies have implicated the JNK pathway in both traumatic and glaucomatous models of optic neuropathy (Sun et al., 2011; Ribas et al., 2011; Bessero et al., 2010; Fernandes et al., 2012). The mechanism by which axonal injury leads to JNK activation in RGC cell bodies, however, has been unclear. The results suggest that DLK may be the as-yet-unidentified trigger for JNK activation and cell death in injured RGCs. Such a role for DLK integrates well with accumulating data about the involvement of DLK in axonal injury and neuronal apoptosis. DLK has been shown to mediate developmental apoptosis in peripheral motor and sensory neurons (Itoh et al., 2011; Ghosh et al., 2011). In adult peripheral neurons, it has been implicated as an important mediator of distal axonal degeneration (Miller et al., 2009) and proximal axonal regeneration (Hammarlund et al., 2009; Yan et al., 2009; Itoh et al., 2009) following axonal injury. It is required for the retrograde transmission of injury mediators like the JNK scaffold protein JIP3 and phosphorylated STAT3, and plays a role in the induction of expression of proregenerative genes (Shin et al., 2012). The work by Watkins et al. suggests that DLK is also involved in the regeneration of optic nerve axons following optic nerve crush. These results, in addition to implicating DLK in neurodegenerative RGC cell death, also raise the possibility that DLK may be important in other forms of CNS neurodegenerative cell loss. The finding that DLK is required for the death of freshly cultured RGCs indicates that DLK does more than just retrograde axonal injury signaling because the cell preparation and purification process completely strips the cells of detectable axonal and dendritic processes. Without wishing to be bound to any one particular theory, it is thought that upregulated DLK contributes to the cell death process directly within the RGC's cell body. An important mechanistic question that remains to be answered is what determines whether activation of DLK signaling leads to primarily axonal regeneration or neuronal cell death and whether these signals can be dissociated.

The JNK signal transduction pathway consists of multiple branches that feed into one or more of the JNKs (Weston and Davis, 2007). One possible approach to RGC neuroprotection is to directly block the pathway downstream with small molecule JNK inhibitors. Such non-specific inhibition of the entire pathway is not an ideal therapeutic strategy, however, since JNK signaling has a number of important physiologic roles, such as tumor suppression (Davies and Tournier, 2012). The finding that the DLK branch is the major pathway leading to proapoptotic JNK activation following RGC injury makes possible a more fine-tuned and specific approach. Additionally, the finding herein that tozasertib is neuroprotective in both glaucoma and traumatic optic neuropathy models can be seen as a proof of principle indicating that the pharmacologic inhibition of DLK signaling may provide a novel, safe, and efficacious approach for glaucoma neuroprotection. The findings also relate to other ocular-related neurodegeneration conditions, such as retinitis pigmentosa, age-related macular degeneration, and the like.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT Patent Application Publication No. WO2010/017541, to Zack et al., for Compositions and Methods for Treatment of Neurodegenerative Disease, published Feb. 11, 2010;

International PCT Patent Application Publication No. WO2011/119777 to Zack et al., for Compositions and Methods for Treatment of Neurodegenerative Disease, published Sep. 29, 2011;

International PCT Patent Application Publication No. WO2011/050192 to Lewcock et al., for Modulation of Axon Degeneration, published Apr. 28, 2011.

International PCT Patent Application Publication No. WO2004/000833 to Charrier et al., for Processes for Preparing Substituted Pyrimidines and Pyrimidine Derivatives as Inhibitors of Protein Kinase, published Dec. 31, 2003;

International PCT Patent Application Publication No. WO2007/056164 to Binch et al., for Aminopyrimidines Useful as Kinase Inhibitors, published May 18, 2007; and International PCT Patent Application Publication No. WO2007/056221 to Binch et al., for Aminopyrimidines Useful as Kinase Inhibitors, published May 18, 2007.

Barres, B. A., Silverstein, B. E., Corey, D. P. & Chun, L. L. Immunological, morphological, and electrophysiological variation among retinal ganglion cells purified by panning. Neuron 1, 791-803 (1988).

Bessero, A.-C., Chiodini, F., Rungger-Brändle, E., Bonny, C. & Clarke, P. G. H. Role of the c-Jun N-terminal kinase pathway in retinal excitotoxicity, and neuroprotection by its inhibition. J. Neurochem. 113, 1307-1318 (2010).

Bhattacharya MRC et al. (2012) A model of toxic neuropathy in Drosophila reveals a role for MORN4 in promoting axonal degeneration. J Neurosci 32:5054-5061.

Bloom, J., Miller, B. R., Sanes, J. R. & DiAntonio, A. The requirement for Phr1 in CNS axon tract formation reveals the corticostriatal boundary as a choice point for cortical axons. Genes Dev. 21, 2593-2606 (2007).

Cohen P (2002) Protein kinases—the major drug targets of the twenty-first century? Nat Rev Drug Discov 1:309-315.

Collins, C. A., Wairkar, Y. P., Johnson, S. L. & DiAntonio, A. Highwire restrains synaptic growth by attenuating a MAP kinase signal. Neuron 51, 57-69 (2006).

Danesh-Meyer, H. V. & Levin, L. A. Neuroprotection: extrapolating from neurologic diseases to the eye. American Journal of Ophthalmology 148, 186-191.e2 (2009).

Davies C, Tournier C (2012) Exploring the function of the JNK (c-Jun N-terminal kinase) signalling pathway in physiological and pathological processes to design novel therapeutic strategies. Biochem Soc Trans 40:85-89.

Davis, M. I. et al. Comprehensive analysis of kinase inhibitor selectivity. Nat. Biotechnol. 29, 1046-1051 (2011).

Dimitriadi M et al. (2010) Conserved Genes Act as Modifiers of Invertebrate SMN Loss of Function Defects. PLoS Genet 6:e1001172.

Edwards, D. A. et al. Large porous particles for pulmonary drug delivery. Science 276, 1868-1871 (1997).

Fernandes, K. A. et al. JNK2 and JNK3 are major regulators of axonal injury-induced retinal ganglion cell death. Neurobiology of Disease (2012).

Ghosh, A. S. et al. DLK induces developmental neuronal degeneration via selective regulation of proapoptotic JNK activity. J. Cell Biol. 194, 751-764 (2011).

Hammarlund M, Nix P, Hauth L, Jorgensen E M, Bastiani M (2009) Axon

Regeneration Requires a Conserved MAP Kinase Pathway. Science 323:802-806.

Harrington E A et al. (2004) VX-680, a potent and selective small-molecule inhibitor of the Aurora kinases, suppresses tumor growth in vivo. Nat Med 10:262-267.

Hisanaga S-I, Endo R (2010) Regulation and role of cyclin-dependent kinase activity in neuronal survival and death. J Neurochem 115:1309-1321.

Inglese, J. et al. Quantitative high-throughput screening: a titration-based approach that efficiently identifies biological activities in large chemical libraries. Proceedings of the National Academy of Sciences of the United States of America 103, 11473-11478 (2006).

Itoh A, Horiuchi M, Bannerman P, Pleasure D, Itoh T (2009) Impaired regenerative response of primary sensory neurons in ZPK/DLK gene-trap mice. Biochem Biophys Res Commun 383:258-262.

Itoh, A. et al. ZPK/DLK, a mitogen-activated protein kinase kinase kinase, is a critical mediator of programmed cell death of motoneurons. J. Neurosci. 31, 7223-7228 (2011).

Karaman, M. W. et al. A quantitative analysis of kinase inhibitor selectivity. Nat. Biotechnol. 26, 127-132 (2008).

Lackey, K. et al. The discovery of potent cRaf1 kinase inhibitors. Bioorganic & Medicinal Chemistry Letters 10, 223-226 (2000).

Levkovitch-Verbin, H. et al. Translimbal laser photocoagulation to the trabecular meshwork as a model of glaucoma in rats. *Investigative Ophthalmology & Visual Science* 43, 402-410 (2002).

Li Y, Schlamp C L, Nickells R W (1999) Experimental induction of retinal ganglion cell death in adult mice. *Investigative Ophthalmology & Visual Science* 40:1004-1008.

Limb G A, Martin K R, the Sixth ARVO/Pfizer Ophthalmics Research Institute Conference Working Group (2011) Current Prospects in Optic Nerve Protection and Regeneration: Sixth ARVO/Pfizer Ophthalmics Research Institute Conference. *Investigative Ophthalmology & Visual Science* 52:5941-5954.

Merritt S E et al. (1999) The mixed lineage kinase DLK utilizes MKK7 and not MKK4 as substrate. *J Biol Chem* 274:10195-10202.

Miller, B. R. et al. A dual leucine kinase-dependent axon self-destruction program promotes Wallerian degeneration. *Nat. Neurosci.* 12, 387-389 (2009).

OFarrell, A. et al. SU11248 is a novel FLT3 tyrosine kinase inhibitor with potent activity in vitro and in vivo. *Blood* 101, 3597-3605 (2003).

Pavlidis M, Fischer D, Thanos S (2000) Photoreceptor degeneration in the RCS rat attenuates dendritic transport and axonal regeneration of ganglion cells. *Investigative Ophthalmology & Visual Science* 41:2318-2328.

Petrs-Silva, H. et al. High-efficiency transduction of the mouse retina by tyrosine-mutant AAV serotype vectors. *Mol. Ther.* 17, 463-471 (2009).

Petrs-Silva, H. et al. Novel properties of tyrosine-mutant AAV2 vectors in the mouse retina. *Mol. Ther.* 19, 293-301 (2011).

Quigley, H. A. & Broman, A. T. The number of people with glaucoma worldwide in 2010 and 2020. *Br J Ophthalmol* 90, 262-267 (2006).

Ribas, V. T., Arruda-Carvalho, M., Linden, R. & Chiarini, L. B. Early c-Jun N-terminal kinase-dependent phosphorylation of activating transcription factor-2 is associated with degeneration of retinal ganglion cells. *Neuroscience* 180, 64-74 (2011).

Robitaille, K. et al. Tissue transglutaminase triggers oligomerization and activation of dual leucine zipper-bearing kinase in calphostin C-treated cells to facilitate apoptosis. *Cell Death Differ* 11, 542-549 (2004).

Satoh K, Fukumoto Y, Shimokawa H (2011) Rho-kinase: important new therapeutic target in cardiovascular diseases. *Am J Physiol Heart Circ Physiol* 301:H287-96.

Schulte J, Sepp K J, Wu C, Hong P, Littleton JT (2011) High-Content Chemical and RNAi Screens for Suppressors of Neurotoxicity in a Huntington's Disease Model. *PLoS ONE* 6:e23841

Scott D L (2011) Role of spleen tyrosine kinase inhibitors in the management of rheumatoid arthritis. *Drugs* 71:1121-1132.

Sharma P, Ando D M, Daub A, Kaye J A, Finkbeiner S (2012) High-throughput screening in primary neurons. *Meth Enzymol* 506:331-360.

Shin J E et al. (2012) Dual Leucine Zipper Kinase Is Required for Retrograde Injury Signaling and Axonal Regeneration. *Neuron* 74:1015-1022.

Subramaniam S, Unsicker K (2010) ERK and cell death: ERK1/2 in neuronal death. *FEBS J* 277:22-29.

Sun, H. et al. Protective effect of a JNK inhibitor against retinal ganglion cell loss induced by acute moderate ocular hypertension. *Mol. Vis.* 17, 864-875 (2011).

Tanaka M, Yanagawa Y, Hirashima N (2009) Transfer of small interfering RNA by single-cell electroporation in cerebellar cell cultures. *Journal of neuroscience methods* 178:80-86.

Tanaka M, Asaoka M, Yanagawa Y, Hirashima N (2011) Long-Term Gene-Silencing Effects of siRNA Introduced by Single-Cell Electroporation into Postmitotic CNS Neurons. *Neurochem Res* 36:1482-1489.

Tang B C, Fu J, Watkins D N, Hanes J (2010) Enhanced efficacy of local etoposide delivery by poly(ether-anhydride) particles against small cell lung cancer in vivo. *Biomaterials* 31:339-344.

Tournier C, Whitmarsh A J, Cavanagh J, Barrett T, Davis R J (1997) Mitogenactivated protein kinase kinase 7 is an activator of the c-Jun NH2-terminal kinase. *Proceedings of the National Academy of Sciences of the United States of America* 94:7337-7342.

Tu W et al. (2010) DAPK1 Interaction with NMDA Receptor NR2B Subunits Mediates Brain Damage in Stroke. *Cell* 140:222-234.

Wang J T, Medress Z A, Ben A Barres Axon degeneration: Molecular mechanisms of a self-destruction pathway.

Weston C R, Davis R J (2007) The JNK signal transduction pathway. *Curr Opin Cell Biol* 19:142-149.

Xiong X et al. (2010) Protein turnover of the Wallenda/DLK kinase regulates a retrograde response to axonal injury. *J Cell Biol* 191:211-223.

Yan D, Wu Z, Chisholm A D, Jin Y (2009) The DLK-1 Kinase Promotes mRNA Stability and Local Translation in *C. elegans* Synapses and Axon Regeneration. *Cell* 138:1005-1018.

Yang Z et al. (2007) Changes in gene expression in experimental glaucoma and optic nerve transection: the equilibrium between protective and detrimental mechanisms. *Investigative Ophthalmology & Visual Science* 48:5539-5548.

Zolotukhin, S. et al. Production and purification of serotype 1, 2, and 5 recombinant adeno-associated viral vectors. *Methods* 28, 158-167 (2002).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating or reducing the probability of developing a neurodegenerative disease, disorder, or condition in a subject in need thereof, the method comprising administering to the subject a therapeutically effective amount of a compound of Formula (I), or a pharmaceutically acceptable salt, hydrate, or prodrug thereof, thereby treating or reducing the probability of developing the neurodegenerative disease, disorder, or condition:

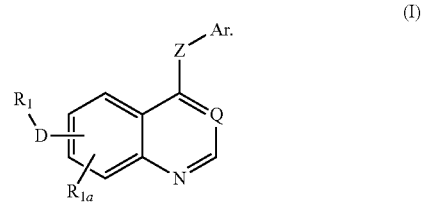

2. The method of claim 1, wherein the compound of Formula (I) is a compound of Formula (XI):

(XI)

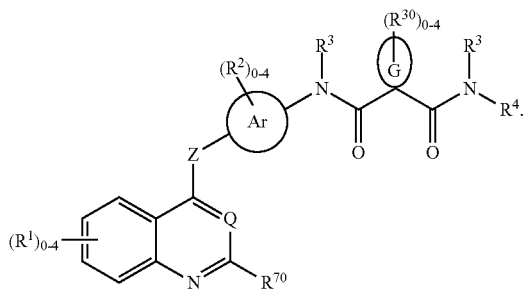

3. The method of claim 1, wherein the compound of Formula (I) is a compound of Formula (XIIIa) or (XIIIb):

(XIIIa)

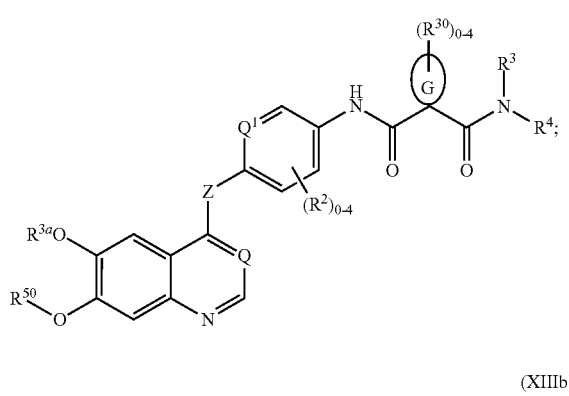

(XIIIb)

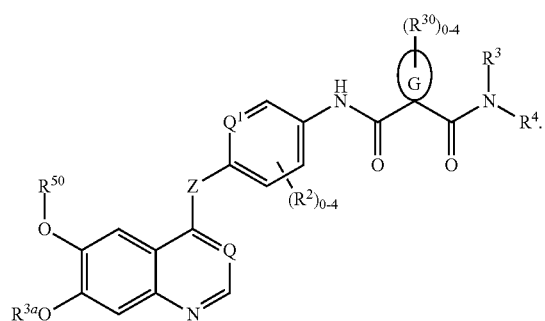

4. The method of claim 1, wherein the compound of Formula (I) is a compound of Formula (XIVa) or Formula (XIVb):

(XIVa)

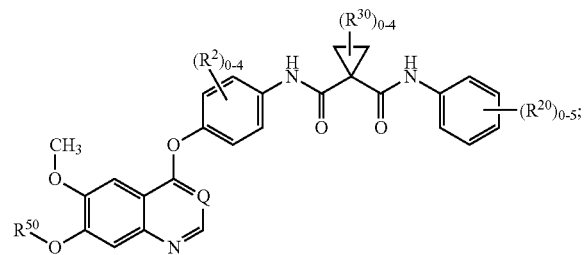

(XIVb)

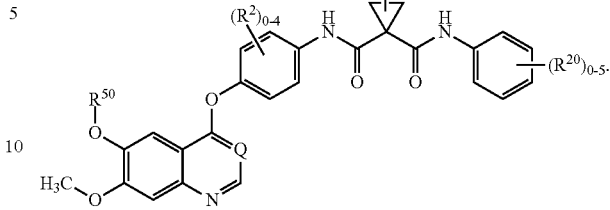

5. The compound of claim 4, wherein the compound of Formula (XIVa) is foretinib.

6. The compound of claim 4, wherein the compound of Formula (XIVb) is cabozantinib.

7. A method for treating or reducing the probability of developing a neurodegenerative disease, disorder, or condition in a subject in need thereof, the method comprising administering to the subject a therapeutically effective amount of a compound selected from the group consisting of crizotinib, KW-2449, bosutinib, axitinib, and dasatinib, thereby treating or reducing the probability of developing the neurodegenerative disease, disorder, or condition.

8. The method of claim 1, wherein the neurodegenerative disease, disorder, or condition is an ocular-related neurodegeneration.

9. The method of claim 8, wherein the ocular-related neurodegeneration is selected from the group consisting of glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis.

10. The method of claim 9, wherein the glaucoma is selected from the group consisting of primary glaucoma, low-tension glaucoma, primary angle-closure glaucoma, acute angle-closure glaucoma, chronic angle-closure glaucoma, intermittent angle-closure glaucoma, chronic open-angle closure glaucoma, pigmentary glaucoma, exfoliation glaucoma, developmental glaucoma, secondary glaucoma, phacogenic glaucoma, glaucoma secondary to intraocular hemorrhage, traumatic glaucoma, neovascular glaucoma, drug-induced glaucoma, toxic glaucoma, and glaucoma associated with intraocular tumors, retinal detachments, severe chemical burns of the eye, and iris atrophy.

11. The method of claim 1, wherein the neurodegenerative disease, disorder, or condition is or is associated with a disease, disorder, or condition of the nervous system selected from the group consisting of amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, AIDS demential complex, alcoholism, Alexander's disease, Alper's disease, ataxia telangiectasia, Batten disease, Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

12. The method of claim 1, wherein the neurodegenerative disease, disorder, or condition comprises one or more conditions that are secondary to a disease, disorder, condition, or therapy having a primary effect outside of the nervous system selected from the group consisting of: peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, yphilis, systemic lupus erythematosus, and amyloidosis.

13. The method of claim 1, wherein the neurodegenerative disease, disorder, or condition is associated with pain selected from the group consisting of chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a torn ligament, and diabetes.

14. The method of claim 1, wherein the neurodegenerative disease, disorder, or condition is associated with one or more injuries to the nervous system.

15. The method of claim 14, wherein the one or more injuries to the nervous system is related to nerve damage caused by exposure to one or more agents selected from the group consisting of toxic compounds, heavy metals, industrial solvents, drugs, chemotherapeutic agents, dapsone, HIV medications, cholesterol lowering drugs, heart or blood pressure medications, and metronidazole.

16. The method of claim 14, wherein the one or more injuries to the nervous system is related to nerve damage caused by one or more conditions selected from the group consisting of burn, wound, surgery, accidents, ischemia, prolonged exposure to cold temperature, stroke, intracranial hemorrhage, and cerebral hemorrhage.

17. The method of claim 1, wherein the neurodegenerative disease, disorder, or condition comprises a psychiatric disorder.

18. The method of claim 17, wherein the psychiatric disorder is selected from the group consisting of schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

19. The method of claim 1, wherein the method promotes or stimulates neurite growth or regeneration from one or more neuronal cells.

20. The method of claim 1, wherein the method comprises treating one or more neuronal cells for a nerve transplantation procedure.

21. The method of claim 20, wherein the treating is before, during, or after the transplantation procedure.

22. The method of claim 1, wherein the method treats or prevents a neuronal cell loss in the subject.

23. The method of claim 1, wherein the method prevents neuronal cell death in the subject.

24. The method of claim 1, wherein the method prevents apoptosis of one or more neuronal axons in the subject.

25. The method of claim 1, wherein an additional therapeutic agent is administered to the subject.

26. The method of claim 25, wherein the additional therapeutic agent is selected from the group consisting of a beta-blocker, an alpha-agonist, a carbonic anhydrase inhibitor, a prostaglandin or a prostaglandin analog, a miotic or a cholinergic agent, an epinephrine compound, forskolin, and one or more additional neuroprotective compounds.

27. The method of claim 1, wherein the compound of Formula (I), or a pharmaceutically acceptable salt thereof, is administered to the subject by a method selected from the group consisting of oral, topical, parenteral, and systemic.

28. A method for promoting retinal ganglion cell (RGC) or photoreceptor cell survival, the method comprising contacting a RGC or photoreceptor cell with at least one compound of Formula (I), or a pharmaceutically acceptable salt, hydrate, or prodrug thereof in an amount sufficient to promote RGC or photoreceptor cell survival:

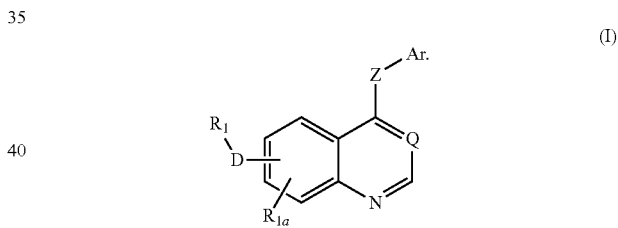

29. The method of claim 28, wherein the method is performed in vitro, in vivo, or ex vivo.

30. The method of claim 28, wherein the compound inhibits the dual-leucine zipper kinase (DLK) pathway.

31. The method of claim 28, wherein the compound inhibits the leucine zipper-bearing kinase (LZK) pathway.

32. A method for identifying injury to an RGC or a photoreceptor cell, the method comprising measuring levels of dual-leucine zipper kinase (DLK) protein in the RGC or photoreceptor cell; and comparing the levels of DLK protein in the RGC or photoreceptor cell to the levels of DLK protein in a control RGC or photoreceptor cell; wherein a significant difference between the levels of DLK protein in the RGC or photoreceptor cell and the levels of DLK protein in the control RGC or photoreceptor cell is indicative of injury to the RGC or photoreceptor cell.

33. A method of identifying injury to an RGC or a photoreceptor cell, the method comprising measuring levels of leucine zipper-bearing kinase (LZK) protein in the RGC or photoreceptor cell; and comparing the levels of LZK protein in the RGC or photoreceptor cell to the levels of LZK protein in a control RGC or photoreceptor cell; wherein a significant difference between the levels of LZK protein in the RGC or photoreceptor cell and the levels of LZK protein in the control RGC or photoreceptor cell is indicative of injury to the RGC or photoreceptor cell.

34. A method of identifying injury to an RGC or a photoreceptor cell in a subject, the method comprising: (a) obtaining a sample from a subject; (b) measuring levels of dual-leucine zipper kinase (DLK) protein and/or leucine zipper-bearing kinase (LZK) protein in the sample; and (c) comparing the levels of DLK protein and/or LZK protein in the sample with the levels of DLK protein and/or LZK protein in a control sample; wherein a significant difference between the levels DLK protein and/or LZK protein in the sample and the levels of DLK protein and/or LZK protein in the control sample is indicative of injury to a RGC or photoreceptor cell in the subject.

35. The method of claim 34, wherein the sample is selected from the group consisting of the vitreous, the aqueous of the eye, and serum.

36. The method of claim 7, wherein the neurodegenerative disease, disorder, or condition is an ocular-related neurodegeneration.

37. The method of claim 36, wherein the ocular-related neurodegeneration is selected from the group consisting of glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis.

38. The method of claim 37, wherein the glaucoma is selected from the group consisting of primary glaucoma, low-tension glaucoma, primary angle-closure glaucoma, acute angle-closure glaucoma, chronic angle-closure glaucoma, intermittent angle-closure glaucoma, chronic open-angle closure glaucoma, pigmentary glaucoma, exfoliation glaucoma, developmental glaucoma, secondary glaucoma, phacogenic glaucoma, glaucoma secondary to intraocular hemorrhage, traumatic glaucoma, neovascular glaucoma, drug-induced glaucoma, toxic glaucoma, and glaucoma associated with intraocular tumors, retinal detachments, severe chemical burns of the eye, and iris atrophy.

* * * * *